United States Patent
Albrecht et al.

(10) Patent No.: US 9,241,697 B2
(45) Date of Patent: Jan. 26, 2016

(54) WOUND RETRACTOR

(71) Applicant: Applied Medical Resources Corporation, Rancho Santa Margarita, CA (US)

(72) Inventors: Jeremy J Albrecht, Rancho Santa Margarita, CA (US); Charles C Hart, Rancho Santa Margarita, CA (US); Eric Nguyen, Rancho Santa Margarita, CA (US); Haruyasu Yawata, Huntington Beach, CA (US); Nabil Hilal, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

(21) Appl. No.: 14/309,043

(22) Filed: Jun. 19, 2014

(65) Prior Publication Data

US 2014/0323812 A1    Oct. 30, 2014

Related U.S. Application Data

(62) Division of application No. 13/467,825, filed on May 9, 2012, now Pat. No. 8,758,236.

(60) Provisional application No. 61/484,362, filed on May 10, 2011.

(51) Int. Cl.
  *A61B 17/02*   (2006.01)
  *A61B 17/34*   (2006.01)

(52) U.S. Cl.
  CPC ......... *A61B 17/0218* (2013.01); *A61B 17/0293* (2013.01); *A61B 17/3423* (2013.01); *A61B 2017/0225* (2013.01); *A61B 2017/0287* (2013.01)

(58) Field of Classification Search
  CPC ........... A61B 17/0218; A61B 17/0293; A61B 2017/0225; A61B 2017/0287
  See application file for complete search history.

(56) References Cited

U.S. PATENT DOCUMENTS 52,014 A    1/1866    Bartlett
202,813 A    4/1878    Hall
(Continued)

FOREIGN PATENT DOCUMENTS

DE    26 05 148 A1    8/1977
DE    33 36 279 C2    1/1986
(Continued)

OTHER PUBLICATIONS

US 5,344,646, Chen (withdrawn).
(Continued)

*Primary Examiner* — Ellen C Hammond
(74) *Attorney, Agent, or Firm* — Cynthia A. Bonner

(57) ABSTRACT

A retraction device for retracting an incision in a body wall includes a sheath that traverses through the incision from outside the body to a body cavity inside the body. The retraction device may include a first, distal retention ring, a second, proximal retention ring, a circumferential, tubular sheath that is coupled to the first and second retention rings, a plurality of tensioning straps, and a proximal lock ring, wherein each of the plurality of straps is coupled to the distal retention ring and extends proximally through the lumen of the sheath and the proximal retention ring. The lock ring is sized and configured to capture the straps between an inner surface of the proximal retention ring and an outer surface of the lock ring. The lock ring is adapted to be positioned within a lumen of the proximal retention ring with the straps exiting between the proximal retention ring and the lock ring. The straps are adapted to be pulled proximally to achieve appropriate tension and subsequent retraction of the incision. The lock ring responds to the tension of the straps by wedging against the inner surface of the proximal retention ring and substantially preventing the straps from slipping distally between the lock ring and the proximal retention ring.

7 Claims, 18 Drawing Sheets

(56) References Cited

U.S. PATENT DOCUMENTS

| | | |
|---|---|---|
| 447,761 A | 3/1891 | Clough |
| 558,364 A | 4/1896 | Doolittle |
| 758,535 A | 4/1904 | Howden |
| 929,583 A | 7/1909 | Gibbs |
| 1,056,966 A | 3/1913 | Belding |
| 1,157,202 A | 10/1915 | Bates et al. |
| 1,221,123 A | 4/1917 | Westhaver |
| 1,242,972 A | 10/1917 | Petit |
| 1,598,284 A | 8/1926 | Kinney |
| 1,690,995 A | 11/1928 | Pratt |
| 1,180,466 A | 6/1931 | Deutsch |
| 1,810,466 A | 6/1931 | Deutsch |
| 2,219,564 A | 10/1940 | Reyniers |
| 2,305,289 A | 12/1942 | Coburg |
| 2,313,164 A | 3/1943 | Nelson |
| 2,478,586 A | 8/1949 | Krapp |
| 2,669,991 A | 2/1954 | Curutchet |
| 2,695,608 A | 11/1954 | Gibbon |
| 2,812,758 A | 11/1957 | Blumenschein |
| 2,835,253 A | 5/1958 | Borgeson |
| 2,853,075 A | 9/1958 | Hoffman et al. |
| 3,039,468 A | 6/1962 | Price |
| 3,057,350 A | 10/1962 | Cowley |
| 3,111,943 A | 11/1963 | Orndorff |
| 3,129,706 A | 4/1964 | Reynolds, Jr. |
| 3,195,934 A | 7/1965 | Parrish |
| 3,244,169 A | 4/1966 | Baxter |
| 3,253,594 A | 5/1966 | Matthews et al. |
| 3,313,299 A | 4/1967 | Spademan |
| 3,329,390 A | 7/1967 | Hulsey |
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 3,402,710 A | 9/1968 | Paleschuck |
| 3,416,520 A | 12/1968 | Creager, Jr. |
| 3,447,533 A | 6/1969 | Spicer |
| 3,522,800 A | 8/1970 | Lesser |
| 3,523,534 A | 8/1970 | Nolan |
| 3,553,862 A | 1/1971 | Hamu |
| 3,570,475 A | 3/1971 | Weinstein |
| 3,656,485 A | 4/1972 | Robertson |
| 3,685,786 A | 8/1972 | Woodson |
| 3,703,896 A | 11/1972 | Nuwayser |
| 3,717,151 A | 2/1973 | Collett |
| 3,717,883 A | 2/1973 | Mosher |
| 3,729,006 A | 4/1973 | Wilder et al. |
| 3,729,045 A | 4/1973 | MacDonald |
| 3,762,080 A | 10/1973 | Poole |
| 3,774,596 A | 11/1973 | Cook |
| 3,782,370 A | 1/1974 | McDonald |
| 3,788,318 A | 1/1974 | Kim et al. |
| 3,789,852 A | 2/1974 | Kim et al. |
| 3,797,478 A | 3/1974 | Walsh et al. |
| 3,799,166 A | 3/1974 | Marsan |
| 3,807,393 A | 4/1974 | McDonald |
| 3,828,764 A | 8/1974 | Jones |
| 3,831,583 A | 8/1974 | Edmunds et al. |
| 3,841,332 A | 10/1974 | Treacle |
| 3,850,172 A | 11/1974 | Cazalis |
| 3,853,126 A | 12/1974 | Schulte |
| 3,853,127 A | 12/1974 | Spademan |
| 3,856,021 A | 12/1974 | McIntosh |
| 3,860,274 A | 1/1975 | Ledstrom et al. |
| 3,861,416 A | 1/1975 | Wichterle |
| 3,863,639 A | 2/1975 | Kleaveland |
| 3,907,389 A | 9/1975 | Cox et al. |
| 3,915,171 A | 10/1975 | Shermeta |
| 3,965,890 A | 6/1976 | Gauthier |
| 3,970,089 A | 7/1976 | Saice |
| 3,996,623 A | 12/1976 | Kaster |
| 4,000,739 A | 1/1977 | Stevens |
| 4,016,884 A | 4/1977 | Kwan-Gett |
| 4,024,872 A | 5/1977 | Muldoon |
| 4,030,500 A | 6/1977 | Ronnquist |
| 4,043,328 A | 8/1977 | Cawood, Jr. et al. |
| 4,069,913 A | 1/1978 | Harrigan |
| 4,082,005 A | 4/1978 | Erdley |
| 4,083,370 A | 4/1978 | Taylor |
| 4,096,853 A | 6/1978 | Weigand |
| 4,112,932 A | 9/1978 | Chiulli |
| 4,130,113 A | 12/1978 | Graham |
| 4,141,364 A | 2/1979 | Schultze |
| 4,177,814 A | 12/1979 | Knepshield et al. |
| 4,183,357 A | 1/1980 | Bentley et al. |
| 4,187,849 A | 2/1980 | Stim |
| 4,188,945 A | 2/1980 | Wenander |
| 4,189,880 A | 2/1980 | Ballin |
| 4,217,664 A | 8/1980 | Faso |
| 4,222,126 A | 9/1980 | Boretos et al. |
| 4,228,792 A | 10/1980 | Rhys-Davies |
| 4,239,036 A | 12/1980 | Krieger |
| 4,240,411 A | 12/1980 | Hosono |
| 4,253,201 A | 3/1981 | Ross et al. |
| 4,254,973 A | 3/1981 | Benjamin |
| 4,306,562 A | 12/1981 | Osborne |
| 4,321,915 A | 3/1982 | Leighton |
| 4,331,138 A | 5/1982 | Jessen |
| 4,338,934 A | 7/1982 | Spademan |
| 4,338,937 A | 7/1982 | Lerman |
| 4,367,728 A | 1/1983 | Mutke |
| 4,369,284 A | 1/1983 | Chen |
| 4,399,816 A | 8/1983 | Spangler |
| 4,402,683 A | 9/1983 | Kopman |
| 4,411,659 A | 10/1983 | Jensen et al. |
| 4,421,296 A | 12/1983 | Stephens |
| 4,424,833 A | 1/1984 | Spector et al. |
| 4,428,364 A | 1/1984 | Bartolo |
| 4,430,081 A | 2/1984 | Timmermans |
| 4,434,791 A | 3/1984 | Darnell |
| 4,436,519 A | 3/1984 | O'Neill |
| 4,454,873 A | 6/1984 | Laufenberg et al. |
| 4,473,067 A | 9/1984 | Schiff |
| 4,475,548 A | 10/1984 | Muto |
| 4,485,490 A | 12/1984 | Akers et al. |
| 4,488,877 A | 12/1984 | Klein |
| 4,543,088 A | 9/1985 | Bootman et al. |
| 4,550,713 A | 11/1985 | Hyman |
| 4,553,537 A | 11/1985 | Rosenberg |
| 4,555,242 A | 11/1985 | Saudagar |
| 4,556,996 A | 12/1985 | Wallace |
| 4,601,710 A | 7/1986 | Moll |
| 4,610,665 A | 9/1986 | Matsumoto et al. |
| 4,626,245 A | 12/1986 | Weinstein |
| 4,634,424 A | 1/1987 | O'Boyle |
| 4,634,432 A | 1/1987 | Kocak |
| 4,644,951 A | 2/1987 | Bays |
| 4,649,904 A | 3/1987 | Krauter |
| 4,653,476 A | 3/1987 | Bonnet |
| 4,654,030 A | 3/1987 | Moll et al. |
| 4,655,752 A | 4/1987 | Honkanen et al. |
| 4,673,393 A | 6/1987 | Suzuki et al. |
| 4,673,394 A | 6/1987 | Fenton |
| 4,691,942 A | 9/1987 | Ford |
| 4,714,749 A | 12/1987 | Hughes et al. |
| 4,738,666 A | 4/1988 | Fuqua |
| 4,755,170 A | 7/1988 | Golden |
| 4,760,933 A | 8/1988 | Christner et al. |
| 4,776,843 A | 10/1988 | Martinez et al. |
| 4,777,943 A | 10/1988 | Chvapil |
| 4,784,646 A | 11/1988 | Feingold |
| 4,796,629 A | 1/1989 | Grayzel |
| 4,798,594 A | 1/1989 | Hillstead |
| 4,802,694 A | 2/1989 | Vargo |
| 4,808,168 A | 2/1989 | Warring |
| 4,809,679 A | 3/1989 | Shimonaka et al. |
| 4,828,554 A | 5/1989 | Griffin |
| 4,842,931 A | 6/1989 | Zook |
| 4,848,575 A | 7/1989 | Nakamura et al. |
| 4,856,502 A | 8/1989 | Ersfeld et al. |
| 4,863,430 A | 9/1989 | Klyce et al. |
| 4,863,438 A | 9/1989 | Gauderer et al. |
| 4,889,107 A | 12/1989 | Kaufman |
| 4,895,565 A | 1/1990 | Hillstead |

(56) References Cited

U.S. PATENT DOCUMENTS

| | | |
|---|---|---|
| 4,897,081 A | 1/1990 | Poirier |
| 4,903,710 A | 2/1990 | Jessamine et al. |
| 4,911,974 A | 3/1990 | Shimizu et al. |
| 4,915,132 A | 4/1990 | Hodge et al. |
| 4,926,882 A | 5/1990 | Lawrence |
| 4,929,235 A | 5/1990 | Merry et al. |
| 4,944,732 A | 7/1990 | Russo |
| 4,950,222 A | 8/1990 | Scott et al. |
| 4,950,223 A | 8/1990 | Silvanov |
| 4,984,564 A | 1/1991 | Yuen |
| 4,991,593 A | 2/1991 | LeVahn |
| 4,998,538 A | 3/1991 | Charowsky et al. |
| 5,000,745 A | 3/1991 | Guest et al. |
| 5,009,224 A | 4/1991 | Cole |
| 5,015,228 A | 5/1991 | Columbus et al. |
| 5,019,101 A | 5/1991 | Purkait et al. |
| 5,026,366 A | 6/1991 | Leckrone |
| 5,037,379 A | 8/1991 | Clayman et al. |
| 5,041,095 A | 8/1991 | Littrell |
| 5,045,070 A | 9/1991 | Grodecki et al. |
| D320,658 S | 10/1991 | Quigley et al. |
| 5,071,411 A | 12/1991 | Hillstead |
| 5,073,169 A | 12/1991 | Raiken |
| 5,074,878 A | 12/1991 | Bark et al. |
| 5,082,005 A | 1/1992 | Kaldany |
| 5,086,763 A | 2/1992 | Hathman |
| 5,092,846 A | 3/1992 | Nishijima et al. |
| 5,104,389 A | 4/1992 | Deem |
| 5,108,420 A | 4/1992 | Marks |
| 5,125,396 A | 6/1992 | Ray |
| 5,125,897 A | 6/1992 | Quinn et al. |
| 5,127,626 A | 7/1992 | Hilal et al. |
| 5,129,885 A | 7/1992 | Green et al. |
| 5,141,498 A | 8/1992 | Christian |
| 5,149,327 A | 9/1992 | Oshiyama |
| 5,156,617 A | 10/1992 | Reid |
| 5,158,553 A | 10/1992 | Berry et al. |
| 5,159,921 A | 11/1992 | Hoover |
| 5,161,773 A | 11/1992 | Tower |
| 5,167,636 A | 12/1992 | Clement |
| 5,167,637 A | 12/1992 | Okada et al. |
| 5,176,648 A | 1/1993 | Holmes et al. |
| 5,176,662 A | 1/1993 | Bartholomew et al. |
| 5,176,697 A | 1/1993 | Hasson et al. |
| 5,178,162 A | 1/1993 | Bose |
| 5,180,365 A | 1/1993 | Ensminger et al. |
| 5,183,471 A | 2/1993 | Wilk |
| 5,188,595 A | 2/1993 | Jacobi |
| 5,188,607 A | 2/1993 | Wu |
| 5,192,301 A | 3/1993 | Kamiya et al. |
| 5,197,955 A | 3/1993 | Stephens et al. |
| 5,207,656 A | 5/1993 | Kranys |
| 5,209,737 A | 5/1993 | Rirchart et al. |
| 5,211,370 A | 5/1993 | Powers |
| 5,211,633 A | 5/1993 | Stouder, Jr. |
| 5,213,114 A | 5/1993 | Bailey, Jr. |
| 5,226,890 A | 7/1993 | Ianniruberto et al. |
| 5,234,455 A | 8/1993 | Mulhollan |
| 5,241,968 A | 9/1993 | Slater |
| 5,242,400 A | 9/1993 | Blake, III et al. |
| 5,242,409 A | 9/1993 | Buelna |
| 5,242,412 A | 9/1993 | Blake, III |
| 5,242,415 A | 9/1993 | Kantrowitz et al. |
| 5,248,304 A | 9/1993 | Vigdorchik et al. |
| 5,256,150 A | 10/1993 | Quiachon et al. |
| 5,257,973 A | 11/1993 | Villasuso |
| 5,257,975 A | 11/1993 | Foshee |
| 5,259,366 A | 11/1993 | Reydel et al. |
| 5,261,883 A | 11/1993 | Hood et al. |
| 5,262,468 A | 11/1993 | Chen |
| 5,263,922 A | 11/1993 | Sova et al. |
| 5,269,763 A | 12/1993 | Boehmer et al. |
| 5,269,772 A | 12/1993 | Wilk |
| 5,273,449 A | 12/1993 | Mattis et al. |
| 5,273,545 A | 12/1993 | Hunt et al. |
| D343,236 S | 1/1994 | Quigley et al. |
| 5,279,575 A | 1/1994 | Sugarbaker |
| 5,290,310 A | 3/1994 | Makower et al. |
| D346,022 S | 4/1994 | Quigley et al. |
| 5,299,582 A | 4/1994 | Potts |
| 5,300,034 A | 4/1994 | Behnke |
| 5,300,035 A | 4/1994 | Clement |
| 5,300,036 A | 4/1994 | Mueller et al. |
| 5,303,486 A | 4/1994 | Dell |
| 5,308,336 A | 5/1994 | Hart et al. |
| 5,309,896 A | 5/1994 | Moll et al. |
| 5,312,391 A | 5/1994 | Wilk |
| 5,314,417 A | 5/1994 | Stephens et al. |
| 5,316,541 A | 5/1994 | Fischer |
| 5,320,611 A | 6/1994 | Bonutti et al. |
| 5,330,437 A | 7/1994 | Durman |
| 5,330,486 A | 7/1994 | Wilk |
| 5,330,497 A | 7/1994 | Freitas et al. |
| 5,331,975 A | 7/1994 | Bonutti |
| 5,334,143 A | 8/1994 | Carroll |
| 5,334,646 A | 8/1994 | Chen |
| 5,336,192 A | 8/1994 | Palestrant |
| 5,336,708 A | 8/1994 | Chen |
| 5,338,313 A | 8/1994 | Mollenauer et al. |
| 5,342,315 A | 8/1994 | Rowe et al. |
| 5,342,385 A | 8/1994 | Norelli et al. |
| 5,350,364 A | 9/1994 | Stephens et al. |
| 5,353,786 A | 10/1994 | Wilk |
| 5,354,280 A | 10/1994 | Haber et al. |
| 5,360,417 A | 11/1994 | Gravener et al. |
| 5,364,345 A | 11/1994 | Lowery et al. |
| 5,364,372 A | 11/1994 | Danks et al. |
| 5,366,446 A | 11/1994 | Tal et al. |
| 5,366,473 A | 11/1994 | Winston et al. |
| 5,366,478 A | 11/1994 | Brinkerhoff et al. |
| 5,368,545 A | 11/1994 | Schaller et al. |
| 5,375,588 A | 12/1994 | Yoon |
| 5,380,288 A | 1/1995 | Hart et al. |
| 5,383,861 A | 1/1995 | Hempel et al. |
| 5,385,552 A | 1/1995 | Haber et al. |
| 5,385,553 A | 1/1995 | Hart et al. |
| 5,385,560 A | 1/1995 | Wulf |
| 5,389,080 A | 2/1995 | Yoon |
| 5,389,081 A | 2/1995 | Castro |
| 5,391,153 A | 2/1995 | Haber et al. |
| 5,391,156 A | 2/1995 | Hildwein et al. |
| 5,395,367 A | 3/1995 | Wilk |
| 5,403,264 A | 4/1995 | Wohlers et al. |
| 5,403,336 A | 4/1995 | Kieturakis et al. |
| 5,407,433 A | 4/1995 | Loomas |
| 5,411,483 A | 5/1995 | Loomas |
| 5,413,571 A | 5/1995 | Katsaros et al. |
| 5,423,848 A | 6/1995 | Washizuka et al. |
| 5,429,609 A | 7/1995 | Yoon |
| 5,431,676 A | 7/1995 | Durdal et al. |
| 5,437,683 A | 8/1995 | Neumann et al. |
| 5,439,455 A | 8/1995 | Kieturakis et al. |
| 5,441,486 A | 8/1995 | Yoon |
| 5,443,452 A | 8/1995 | Hart et al. |
| 5,454,365 A | 10/1995 | Bonutti |
| 5,456,284 A | 10/1995 | Ryan et al. |
| 5,460,170 A | 10/1995 | Hammerslag |
| 5,460,616 A | 10/1995 | Weinstein et al. |
| 5,468,248 A | 11/1995 | Chin et al. |
| 5,476,475 A | 12/1995 | Gadberry |
| 5,480,410 A | 1/1996 | Cuschieri et al. |
| 5,486,426 A | 1/1996 | McGee et al. |
| 5,490,843 A | 2/1996 | Hildwein et al. |
| 5,492,304 A | 2/1996 | Smith et al. |
| 5,496,280 A | 3/1996 | Vandenbroek et al. |
| 5,503,112 A | 4/1996 | Luhman et al. |
| 5,507,758 A | 4/1996 | Thomason et al. |
| 5,508,334 A | 4/1996 | Chen |
| 5,511,564 A | 4/1996 | Wilk |
| 5,514,109 A | 5/1996 | Mollenauer et al. |
| 5,514,133 A | 5/1996 | Golub et al. |
| 5,514,153 A | 5/1996 | Bonutti |
| 5,518,278 A | 5/1996 | Sampson |
| 5,520,632 A | 5/1996 | Leveen |

(56) References Cited

U.S. PATENT DOCUMENTS

| | | |
|---|---|---|
| 5,522,791 A | 6/1996 | Leyva |
| 5,522,824 A | 6/1996 | Ashby |
| 5,524,644 A | 6/1996 | Crook |
| 5,526,536 A | 6/1996 | Cartmill |
| 5,531,758 A | 7/1996 | Uschold et al. |
| 5,538,509 A | 7/1996 | Dunlap et al. |
| 5,540,648 A | 7/1996 | Yoon |
| 5,540,711 A | 7/1996 | Kieturakis et al. |
| 5,545,150 A | 8/1996 | Danks et al. |
| 5,545,179 A | 8/1996 | Williamson, IV |
| 5,549,563 A | 8/1996 | Kronner |
| 5,549,637 A | 8/1996 | Crainich |
| 5,554,124 A | 9/1996 | Alvarado |
| 5,555,653 A | 9/1996 | Morgan |
| 5,562,632 A | 10/1996 | Davila et al. |
| 5,562,677 A | 10/1996 | Hildwein et al. |
| 5,562,688 A | 10/1996 | Riza |
| 5,571,115 A | 11/1996 | Nicholas |
| 5,571,137 A | 11/1996 | Marlow et al. |
| 5,575,799 A | 11/1996 | Bolanos et al. |
| 5,577,993 A | 11/1996 | Zhu et al. |
| 5,578,048 A | 11/1996 | Pasqualucci et al. |
| 5,580,344 A | 12/1996 | Hasson |
| 5,584,850 A | 12/1996 | Hart et al. |
| 5,601,579 A | 2/1997 | Semertzides |
| 5,601,581 A | 2/1997 | Fogarty et al. |
| 5,603,702 A | 2/1997 | Smith et al. |
| 5,607,443 A | 3/1997 | Kieturakis et al. |
| 5,620,415 A | 4/1997 | Lucey et al. |
| 5,620,420 A | 4/1997 | Kriesel |
| 5,628,732 A | 5/1997 | Antoon, Jr. et al. |
| 5,632,284 A | 5/1997 | Graether |
| 5,632,979 A | 5/1997 | Goldberg et al. |
| 5,634,911 A | 6/1997 | Hermann et al. |
| 5,634,936 A | 6/1997 | Linden et al. |
| 5,634,937 A | 6/1997 | Mollenauer et al. |
| 5,636,645 A | 6/1997 | Ou |
| 5,640,977 A | 6/1997 | Leahy et al. |
| 5,643,301 A | 7/1997 | Mollenauer |
| 5,649,550 A | 7/1997 | Crook |
| 5,651,771 A | 7/1997 | Tangherlini et al. |
| 5,653,705 A | 8/1997 | de la Torre et al. |
| 5,657,963 A | 8/1997 | Hinchliffe et al. |
| 5,658,272 A | 8/1997 | Hasson |
| 5,658,306 A | 8/1997 | Kieturakis |
| 5,662,615 A | 9/1997 | Blake, III |
| 5,672,168 A | 9/1997 | de la Torre et al. |
| 5,681,341 A | 10/1997 | Lunsford et al. |
| 5,683,378 A | 11/1997 | Christy |
| 5,685,854 A | 11/1997 | Green et al. |
| 5,685,857 A | 11/1997 | Negus et al. |
| 5,697,914 A | 12/1997 | Brimhall |
| 5,707,703 A | 1/1998 | Rothrum et al. |
| 5,709,664 A | 1/1998 | Vandenbroek et al. |
| 5,713,858 A | 2/1998 | Heruth et al. |
| 5,713,869 A | 2/1998 | Morejon |
| 5,720,730 A | 2/1998 | Blake, III |
| 5,725,536 A | 3/1998 | Oberlin et al. |
| 5,728,103 A | 3/1998 | Picha et al. |
| 5,730,748 A | 3/1998 | Fogarty et al. |
| 5,735,791 A | 4/1998 | Alexander et al. |
| 5,738,628 A | 4/1998 | Sierocuk et al. |
| 5,741,234 A | 4/1998 | Aboul-Hosn |
| 5,741,298 A | 4/1998 | MacLeod |
| 5,743,884 A | 4/1998 | Hasson et al. |
| 5,749,882 A | 5/1998 | Hart et al. |
| 5,753,150 A | 5/1998 | Martin et al. |
| 5,755,660 A | 5/1998 | Tyagi |
| 5,760,117 A | 6/1998 | Chen |
| 5,769,783 A | 6/1998 | Fowler |
| 5,782,812 A | 7/1998 | Hart et al. |
| 5,782,817 A | 7/1998 | Franzel et al. |
| 5,782,859 A | 7/1998 | Nicholas et al. |
| 5,788,676 A | 8/1998 | Yoon |
| 5,792,119 A | 8/1998 | Marx |
| 5,794,528 A | 8/1998 | Gronig et al. |
| 5,795,290 A | 8/1998 | Bridges |
| 5,803,919 A | 9/1998 | Hart et al. |
| 5,803,921 A | 9/1998 | Bonadio |
| 5,803,923 A | 9/1998 | Singh-Derewa et al. |
| 5,807,350 A | 9/1998 | Diaz |
| 5,810,712 A | 9/1998 | Dunn |
| 5,810,721 A | 9/1998 | Mueller et al. |
| 5,813,409 A | 9/1998 | Leahy et al. |
| 5,814,026 A | 9/1998 | Yoon |
| 5,817,062 A | 10/1998 | Flom et al. |
| 5,819,375 A | 10/1998 | Kastner |
| 5,820,555 A | 10/1998 | Watkins, III et al. |
| 5,820,600 A | 10/1998 | Carlson et al. |
| 5,830,191 A | 11/1998 | Hildwein et al. |
| 5,832,925 A | 11/1998 | Rothrum |
| 5,836,871 A | 11/1998 | Wallace et al. |
| 5,841,298 A | 11/1998 | Huang |
| 5,842,971 A | 12/1998 | Yoon |
| 5,848,992 A | 12/1998 | Hart et al. |
| 5,853,395 A | 12/1998 | Crook et al. |
| 5,853,417 A | 12/1998 | Fogarty et al. |
| 5,857,461 A | 1/1999 | Levitsky et al. |
| 5,860,995 A | 1/1999 | Berkelaar |
| 5,865,728 A | 2/1999 | Moll et al. |
| 5,865,729 A | 2/1999 | Meehan et al. |
| 5,865,807 A | 2/1999 | Blake, III |
| 5,865,817 A | 2/1999 | Moenning et al. |
| 5,871,474 A | 2/1999 | Hermann et al. |
| 5,876,413 A | 3/1999 | Fogarty et al. |
| 5,879,368 A | 3/1999 | Hoskin et al. |
| 5,882,344 A | 3/1999 | Stouder, Jr. |
| 5,884,639 A | 3/1999 | Chen |
| 5,894,843 A | 4/1999 | Benetti et al. |
| 5,895,377 A | 4/1999 | Smith et al. |
| 5,899,208 A | 5/1999 | Bonadio |
| 5,899,913 A | 5/1999 | Fogarty et al. |
| 5,904,703 A | 5/1999 | Gilson |
| 5,906,577 A | 5/1999 | Beane et al. |
| 5,913,847 A | 6/1999 | Yoon |
| 5,916,198 A | 6/1999 | Dillow |
| 5,916,232 A | 6/1999 | Hart |
| 5,919,476 A | 7/1999 | Fischer et al. |
| 5,931,832 A | 8/1999 | Jensen |
| 5,947,922 A | 9/1999 | MacLeod |
| 5,951,467 A | 9/1999 | Picha et al. |
| 5,951,588 A | 9/1999 | Moenning |
| 5,957,888 A | 9/1999 | Hinchliffe et al. |
| 5,957,913 A | 9/1999 | de la Torre et al. |
| 5,961,539 A | 10/1999 | Northrup, III et al. |
| 5,962,572 A | 10/1999 | Chen |
| 5,964,781 A | 10/1999 | Mollenauer et al. |
| 5,976,174 A | 11/1999 | Ruiz |
| 5,989,232 A | 11/1999 | Yoon |
| 5,989,233 A | 11/1999 | Yoon |
| 5,989,266 A | 11/1999 | Foster |
| 5,993,471 A | 11/1999 | Riza et al. |
| 5,993,485 A | 11/1999 | Beckers |
| 5,993,839 A | 11/1999 | Mixon |
| 5,994,450 A | 11/1999 | Pearce |
| 5,997,515 A | 12/1999 | de la Torre et al. |
| 6,004,303 A | 12/1999 | Peterson |
| 6,010,494 A | 1/2000 | Schafer et al. |
| 6,017,355 A | 1/2000 | Hessel et al. |
| 6,018,094 A | 1/2000 | Fox |
| 6,024,736 A | 2/2000 | de la Torre et al. |
| 6,025,067 A | 2/2000 | Fay |
| 6,033,426 A | 3/2000 | Kaji |
| 6,033,428 A | 3/2000 | Sardella |
| 6,035,559 A | 3/2000 | Freed et al. |
| 6,042,573 A | 3/2000 | Lucey |
| 6,045,535 A | 4/2000 | Ben Nun |
| 6,048,309 A | 4/2000 | Flom et al. |
| 6,050,871 A | 4/2000 | Chen |
| 6,053,934 A | 4/2000 | Andrews et al. |
| 6,059,806 A | 5/2000 | Hoegerle |
| 6,066,117 A | 5/2000 | Fox et al. |
| 6,068,639 A | 5/2000 | Fogarty et al. |
| 6,077,288 A | 6/2000 | Shimomura |

(56) References Cited

U.S. PATENT DOCUMENTS

| | | |
|---|---|---|
| 6,086,603 A | 7/2000 | Termin et al. |
| 6,090,043 A | 7/2000 | Austin et al. |
| 6,099,506 A | 8/2000 | Macoviak et al. |
| 6,110,154 A | 8/2000 | Shimomura et al. |
| 6,123,689 A | 9/2000 | To |
| 6,142,935 A | 11/2000 | Flom et al. |
| 6,142,936 A | 11/2000 | Beane et al. |
| 6,149,642 A | 11/2000 | Gerhart et al. |
| 6,150,608 A | 11/2000 | Wambeke et al. |
| 6,154,991 A | 12/2000 | Duncan et al. |
| 6,159,182 A | 12/2000 | Davis |
| 6,162,172 A | 12/2000 | Cosgrove et al. |
| 6,162,196 A | 12/2000 | Hart et al. |
| 6,162,206 A | 12/2000 | Bindokas |
| 6,163,949 A | 12/2000 | Neuenschwander |
| 6,164,279 A | 12/2000 | Tweedle |
| 6,171,282 B1 | 1/2001 | Ragsdale |
| 6,183,486 B1 | 2/2001 | Snow et al. |
| 6,197,002 B1 | 3/2001 | Peterson |
| 6,217,555 B1 | 4/2001 | Hart et al. |
| 6,217,590 B1 | 4/2001 | Levinson |
| 6,224,612 B1 | 5/2001 | Bates et al. |
| 6,228,063 B1 | 5/2001 | Aboul-Hosn |
| 6,238,373 B1 | 5/2001 | de la Torre et al. |
| 6,241,768 B1 | 6/2001 | Agarwal et al. |
| 6,254,533 B1 | 7/2001 | Fadem et al. |
| 6,254,534 B1 | 7/2001 | Butler et al. |
| 6,258,065 B1 | 7/2001 | Dennis et al. |
| 6,264,604 B1 | 7/2001 | Kieturakis et al. |
| 6,267,751 B1 | 7/2001 | Mangosong |
| 6,276,661 B1 | 8/2001 | Laird |
| 6,287,280 B1 | 9/2001 | Lampropoulos et al. |
| 6,315,770 B1 | 11/2001 | de la Torre et al. |
| 6,319,246 B1 | 11/2001 | de la Torre et al. |
| 6,322,541 B2 | 11/2001 | West |
| 6,325,384 B1 | 12/2001 | Berry, Sr. et al. |
| 6,346,074 B1 | 2/2002 | Roth |
| 6,355,052 B1 | 3/2002 | Neuss et al. |
| 6,371,968 B1 | 4/2002 | Kogasaka et al. |
| 6,378,944 B1 | 4/2002 | Weisser |
| 6,382,211 B1 | 5/2002 | Crook |
| 6,383,162 B1 | 5/2002 | Sugarbaker |
| 6,391,043 B1 | 5/2002 | Moll et al. |
| 6,413,244 B1 | 7/2002 | Bestetti et al. |
| 6,413,458 B1 | 7/2002 | Pearce |
| 6,420,475 B1 | 7/2002 | Chen |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,482,181 B1 | 11/2002 | Racenet et al. |
| 6,482,227 B1 | 11/2002 | Solovay |
| 6,485,435 B1 | 11/2002 | Bakal |
| 6,485,467 B1 | 11/2002 | Crook et al. |
| 6,488,620 B1 | 12/2002 | Segermark et al. |
| 6,488,692 B1 | 12/2002 | Spence et al. |
| 6,494,893 B2 | 12/2002 | Dubrul et al. |
| 6,527,787 B1 | 3/2003 | Fogarty et al. |
| 6,533,734 B1 | 3/2003 | Corley, III et al. |
| 6,551,270 B1 | 4/2003 | Bimbo et al. |
| 6,551,276 B1 | 4/2003 | Mann et al. |
| 6,551,344 B2 | 4/2003 | Thill |
| 6,552,109 B1 | 4/2003 | Chen |
| 6,554,793 B1 | 4/2003 | Pauker et al. |
| 6,558,371 B2 | 5/2003 | Dorn |
| 6,560,782 B2 | 5/2003 | Hourihan et al. |
| 6,569,120 B1 | 5/2003 | Green |
| 6,578,577 B2 | 6/2003 | Bonadio et al. |
| 6,579,281 B2 | 6/2003 | Palmer et al. |
| 6,582,364 B2 | 6/2003 | Butler et al. |
| 6,585,773 B1 | 7/2003 | Xie |
| 6,589,167 B1 | 7/2003 | Shimomura et al. |
| 6,589,211 B1 | 7/2003 | MacLeod |
| 6,607,504 B2 | 8/2003 | Haarala et al. |
| 6,613,952 B2 | 9/2003 | Rambo |
| 6,623,426 B2 | 9/2003 | Bonadio et al. |
| 6,627,275 B1 | 9/2003 | Chen |
| 6,663,598 B1 | 12/2003 | Carrillo et al. |
| 6,669,674 B1 | 12/2003 | Macoviak et al. |
| 6,676,639 B1 | 1/2004 | Ternström |
| 6,702,787 B2 | 3/2004 | Racenet et al. |
| 6,705,989 B2 | 3/2004 | Cuschieri et al. |
| 6,706,050 B1 | 3/2004 | Giannadakis |
| 6,714,298 B2 | 3/2004 | Ryer |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,793,621 B2 | 9/2004 | Butler et al. |
| 6,794,440 B2 | 9/2004 | Chen |
| 6,796,940 B2 | 9/2004 | Bonadio et al. |
| 6,797,765 B2 | 9/2004 | Pearce |
| 6,800,084 B2 | 10/2004 | Davison et al. |
| 6,811,546 B1 | 11/2004 | Callas et al. |
| 6,814,078 B2 | 11/2004 | Crook |
| 6,814,700 B1 | 11/2004 | Mueller et al. |
| 6,817,974 B2 | 11/2004 | Cooper et al. |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,860,463 B2 | 3/2005 | Hartley |
| 6,863,674 B2 | 3/2005 | Kasahara et al. |
| 6,866,861 B1 | 3/2005 | Luhman |
| 6,867,253 B1 | 3/2005 | Chen |
| 6,869,393 B2 | 3/2005 | Butler |
| 6,878,110 B2 | 4/2005 | Yang et al. |
| 6,884,253 B1 | 4/2005 | McFarlane |
| 6,890,295 B2 | 5/2005 | Michels et al. |
| 6,895,965 B2 | 5/2005 | Scarberry et al. |
| 6,901,870 B2 | 6/2005 | Eklof et al. |
| 6,902,541 B2 | 6/2005 | McNally et al. |
| 6,902,569 B2 | 6/2005 | Parmer et al. |
| 6,908,430 B2 | 6/2005 | Caldwell et al. |
| 6,909,220 B2 | 6/2005 | Chen |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,936,005 B2 | 8/2005 | Poff et al. |
| 6,936,037 B2 | 8/2005 | Bubb et al. |
| 6,939,296 B2 | 9/2005 | Ewers et al. |
| 6,945,932 B1 | 9/2005 | Caldwell et al. |
| 6,958,037 B2 | 10/2005 | Ewers et al. |
| 6,958,069 B2 | 10/2005 | Shipp et al. |
| 6,972,026 B1 | 12/2005 | Caldwell et al. |
| 6,979,324 B2 | 12/2005 | Bybordi et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,014,628 B2 | 3/2006 | Bousquet |
| 7,033,319 B2 | 4/2006 | Pulford et al. |
| 7,041,056 B2 | 5/2006 | Deslauriers et al. |
| 7,052,454 B2 | 5/2006 | Taylor |
| 7,056,304 B2 | 6/2006 | Bacher et al. |
| 7,056,321 B2 | 6/2006 | Pagliuca et al. |
| 7,067,583 B2 | 6/2006 | Chen |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,093,599 B2 | 8/2006 | Chen |
| 7,100,614 B2 | 9/2006 | Stevens et al. |
| 7,101,353 B2 | 9/2006 | Lui et al. |
| 7,105,009 B2 | 9/2006 | Johnson |
| 7,105,607 B2 | 9/2006 | Chen |
| 7,112,185 B2 | 9/2006 | Hart et al. |
| 7,118,528 B1 | 10/2006 | Piskun |

(56) References Cited

U.S. PATENT DOCUMENTS

| | | |
|---|---|---|
| 7,134,929 B2 | 11/2006 | Chen |
| 7,153,261 B2 | 12/2006 | Wenchell |
| 7,163,510 B2 | 1/2007 | Kahle et al. |
| 7,192,436 B2 | 3/2007 | Sing et al. |
| 7,193,002 B2 | 3/2007 | Chen |
| 7,195,590 B2 | 3/2007 | Butler et al. |
| 7,214,185 B1 | 5/2007 | Rosney et al. |
| 7,217,277 B2 | 5/2007 | Parihar et al. |
| 7,222,380 B2 | 5/2007 | Chen |
| 7,223,257 B2 | 5/2007 | Shubayev et al. |
| 7,223,278 B2 | 5/2007 | Davison et al. |
| 7,226,484 B2 | 6/2007 | Chen |
| 7,235,062 B2 | 6/2007 | Brustad |
| 7,235,084 B2 | 6/2007 | Skakoon et al. |
| 7,238,154 B2 | 7/2007 | Ewers et al. |
| 7,244,244 B2 | 7/2007 | Racenet et al. |
| 7,276,075 B1 | 10/2007 | Callas et al. |
| 7,290,367 B2 | 11/2007 | Chen |
| 7,294,103 B2 | 11/2007 | Bertolero et al. |
| 7,297,106 B2 | 11/2007 | Yamada et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,338,473 B2 | 3/2008 | Campbell et al. |
| 7,344,546 B2 | 3/2008 | Wulfman et al. |
| 7,344,547 B2 | 3/2008 | Piskun |
| 7,344,568 B2 | 3/2008 | Chen |
| 7,377,898 B2 | 5/2008 | Ewers et al. |
| 7,390,317 B2 | 6/2008 | Taylor et al. |
| 7,393,322 B2 | 7/2008 | Wenchell |
| 7,412,977 B2 | 8/2008 | Fields et al. |
| 7,445,597 B2 | 11/2008 | Butler et al. |
| 7,473,221 B2 | 1/2009 | Ewers et al. |
| 7,481,765 B2 | 1/2009 | Ewers et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,578,832 B2 | 8/2009 | Johnson |
| 7,645,232 B2 | 1/2010 | Shluzas |
| 7,650,887 B2 | 1/2010 | Nguyen et al. |
| 7,661,164 B2 | 2/2010 | Chen |
| 7,704,207 B2 | 4/2010 | Albrecht et al. |
| 7,717,847 B2 | 5/2010 | Smith |
| 7,727,146 B2 | 6/2010 | Albrecht et al. |
| 7,727,225 B2 | 6/2010 | Broaddus et al. |
| 7,736,306 B2 | 6/2010 | Brustad et al. |
| 7,749,415 B2 | 7/2010 | Brustad et al. |
| 7,753,901 B2 | 7/2010 | Piskun et al. |
| 7,758,500 B2 | 7/2010 | Boyd et al. |
| 7,766,824 B2 | 8/2010 | Jensen et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,850,667 B2 | 12/2010 | Gresham |
| 7,867,164 B2 | 1/2011 | Butler et al. |
| 7,878,974 B2 | 2/2011 | Brustad et al. |
| 7,896,889 B2 | 3/2011 | Mazzocchi et al. |
| 7,909,760 B2 | 3/2011 | Albrecht et al. |
| 7,930,782 B2 | 4/2011 | Chen |
| 2001/0037053 A1 | 11/2001 | Bonadio et al. |
| 2001/0047188 A1 | 11/2001 | Bonadio et al. |
| 2002/0002324 A1 | 1/2002 | McManus |
| 2002/0010389 A1 | 1/2002 | Butler et al. |
| 2002/0013542 A1 | 1/2002 | Bonadio et al. |
| 2002/0016607 A1 | 2/2002 | Bonadio et al. |
| 2002/0026230 A1 | 2/2002 | Moll et al. |
| 2002/0038077 A1 | 3/2002 | de la Torre et al. |
| 2002/0072762 A1 | 6/2002 | Bonadio et al. |
| 2002/0111536 A1 | 8/2002 | Cuschieri et al. |
| 2002/0156432 A1 | 10/2002 | Racenet |
| 2002/0162559 A1 | 11/2002 | Crook |
| 2003/0004253 A1 | 1/2003 | Chen |
| 2003/0014076 A1 | 1/2003 | Mollenauer et al. |
| 2003/0028179 A1 | 2/2003 | Piskun |
| 2003/0040711 A1 | 2/2003 | Racenet et al. |
| 2003/0059865 A1 | 3/2003 | Nelson |
| 2003/0078476 A1 | 4/2003 | Hill |
| 2003/0078478 A1 | 4/2003 | Bonadio et al. |
| 2003/0139756 A1 | 7/2003 | Brustad |
| 2003/0167040 A1 | 9/2003 | Bacher et al. |
| 2003/0187376 A1 | 10/2003 | Rambo |
| 2003/0191371 A1 | 10/2003 | Smith et al. |
| 2003/0192553 A1 | 10/2003 | Rambo |
| 2003/0225392 A1 | 12/2003 | McMichael et al. |
| 2003/0236505 A1 | 12/2003 | Bonadio et al. |
| 2003/0236549 A1 | 12/2003 | Bonadio et al. |
| 2004/0015185 A1 | 1/2004 | Ewers et al. |
| 2004/0024363 A1 | 2/2004 | Goldberg |
| 2004/0049099 A1 | 3/2004 | Ewers et al. |
| 2004/0049100 A1 | 3/2004 | Butler |
| 2004/0054353 A1 | 3/2004 | Taylor |
| 2004/0063833 A1 | 4/2004 | Chen |
| 2004/0068232 A1 | 4/2004 | Hart et al. |
| 2004/0070187 A1 | 4/2004 | Chen |
| 2004/0072942 A1 | 4/2004 | Chen |
| 2004/0073090 A1 | 4/2004 | Butler |
| 2004/0092795 A1 | 5/2004 | Bonadio et al. |
| 2004/0092796 A1 | 5/2004 | Butler et al. |
| 2004/0093018 A1 | 5/2004 | Johnson |
| 2004/0097793 A1 | 5/2004 | Butler et al. |
| 2004/0106942 A1 | 6/2004 | Taylor |
| 2004/0111061 A1 | 6/2004 | Curran |
| 2004/0127772 A1 | 7/2004 | Ewers et al. |
| 2004/0138529 A1 | 7/2004 | Wiltshire et al. |
| 2004/0143158 A1 | 7/2004 | Hart et al. |
| 2004/0154624 A1 | 8/2004 | Bonadio et al. |
| 2004/0167559 A1 | 8/2004 | Taylor et al. |
| 2004/0173218 A1 | 9/2004 | Yamada et al. |
| 2004/0215063 A1 | 10/2004 | Bonadio et al. |
| 2004/0230161 A1 | 11/2004 | Zeiner |
| 2004/0243144 A1 | 12/2004 | Bonadio et al. |
| 2004/0249248 A1 | 12/2004 | Bonadio et al. |
| 2004/0254426 A1 | 12/2004 | Wenchell |
| 2004/0260244 A1 | 12/2004 | Piechowicz et al. |
| 2004/0267096 A1 | 12/2004 | Caldwell et al. |
| 2005/0020884 A1 | 1/2005 | Hart et al. |
| 2005/0033246 A1 | 2/2005 | Ahlbert et al. |
| 2005/0033327 A1 | 2/2005 | Gainor et al. |
| 2005/0059865 A1 | 3/2005 | Kahle et al. |
| 2005/0065475 A1 | 3/2005 | Hart et al. |
| 2005/0065543 A1 | 3/2005 | Kahle et al. |
| 2005/0080319 A1 | 4/2005 | Dinkler, II et al. |
| 2005/0090713 A1 | 4/2005 | Gonzales et al. |
| 2005/0090716 A1 | 4/2005 | Bonadio et al. |
| 2005/0090717 A1 | 4/2005 | Bonadio et al. |
| 2005/0096695 A1 | 5/2005 | Olich |
| 2005/0131349 A1 | 6/2005 | Albrecht et al. |
| 2005/0148823 A1 | 7/2005 | Vaugh et al. |
| 2005/0155611 A1 | 7/2005 | Vaugh et al. |
| 2005/0159647 A1 | 7/2005 | Hart et al. |
| 2005/0159650 A1 | 7/2005 | Raymond et al. |
| 2005/0165281 A1 | 7/2005 | Ravikumar et al. |
| 2005/0192483 A1 | 9/2005 | Bonadio et al. |
| 2005/0192598 A1 | 9/2005 | Johnson et al. |
| 2005/0197537 A1 | 9/2005 | Bonadio et al. |
| 2005/0203346 A1 | 9/2005 | Bonadio et al. |
| 2005/0209510 A1 | 9/2005 | Bonadio et al. |
| 2005/0215863 A1 | 9/2005 | Ravikumar et al. |
| 2005/0222582 A1 | 10/2005 | Wenchell |
| 2005/0228447 A1 | 10/2005 | Rambo |
| 2005/0240082 A1 | 10/2005 | Bonadio et al. |
| 2005/0241647 A1 | 11/2005 | Nguyen |
| 2005/0251124 A1 | 11/2005 | Zvuloni et al. |
| 2005/0261720 A1 | 11/2005 | Caldwell et al. |
| 2005/0267419 A1 | 12/2005 | Smith |
| 2005/0277946 A1 | 12/2005 | Greenhalgh |
| 2005/0283050 A1 | 12/2005 | Gundlapalli et al. |
| 2005/0288558 A1 | 12/2005 | Ewers et al. |
| 2005/0288634 A1 | 12/2005 | O'Heeron et al. |
| 2006/0020164 A1 | 1/2006 | Butler et al. |
| 2006/0020241 A1 | 1/2006 | Piskun et al. |
| 2006/0030755 A1 | 2/2006 | Ewers et al. |
| 2006/0041270 A1 | 2/2006 | Lenker |
| 2006/0047284 A1 | 3/2006 | Gresham |

(56) References Cited

U.S. PATENT DOCUMENTS

| | | |
|---|---|---|
| 2006/0047293 A1 | 3/2006 | Haberland et al. |
| 2006/0052669 A1 | 3/2006 | Hart |
| 2006/0084842 A1 | 4/2006 | Hart et al. |
| 2006/0106402 A1 | 5/2006 | McLucas |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh, II et al. |
| 2006/0258899 A1 | 11/2006 | Gill et al. |
| 2006/0264706 A1 | 11/2006 | Piskun |
| 2006/0270911 A1 | 11/2006 | Voegele et al. |
| 2007/0004968 A1 | 1/2007 | Bonadio et al. |
| 2007/0049966 A1 | 3/2007 | Bonadio et al. |
| 2007/0088202 A1 | 4/2007 | Albrecht et al. |
| 2007/0093695 A1 | 4/2007 | Bonadio et al. |
| 2007/0118175 A1 | 5/2007 | Butler et al. |
| 2007/0149859 A1 | 6/2007 | Albrecht et al. |
| 2007/0151566 A1 | 7/2007 | Kahle et al. |
| 2007/0156023 A1 | 7/2007 | Frasier et al. |
| 2007/0203398 A1 | 8/2007 | Bonadio et al. |
| 2007/0208312 A1 | 9/2007 | Norton et al. |
| 2007/0255219 A1 | 11/2007 | Vaugh et al. |
| 2007/0270654 A1 | 11/2007 | Pignato et al. |
| 2007/0299387 A1 | 12/2007 | Williams et al. |
| 2008/0027476 A1 | 1/2008 | Piskun |
| 2008/0048011 A1 | 2/2008 | Weller |
| 2008/0097162 A1 | 4/2008 | Bonadio et al. |
| 2008/0097163 A1 | 4/2008 | Butler et al. |
| 2008/0103366 A1 | 5/2008 | Banchieri et al. |
| 2008/0200767 A1 | 8/2008 | Ewers et al. |
| 2008/0255519 A1 | 10/2008 | Piskun et al. |
| 2008/0281161 A1 | 11/2008 | Albrecht et al. |
| 2008/0281162 A1 | 11/2008 | Albrecht et al. |
| 2009/0012477 A1 | 1/2009 | Norton et al. |
| 2009/0036745 A1 | 2/2009 | Bonadio et al. |
| 2009/0069837 A1 | 3/2009 | Bonadio et al. |
| 2009/0093683 A1 | 4/2009 | Richard et al. |
| 2009/0093752 A1 | 4/2009 | Richard et al. |
| 2009/0131754 A1 | 5/2009 | Ewers et al. |
| 2009/0137879 A1 | 5/2009 | Ewers et al. |
| 2009/0149714 A1 | 6/2009 | Bonadio |
| 2009/0182279 A1 | 7/2009 | Wenchell et al. |
| 2009/0187079 A1 | 7/2009 | Albrecht et al. |
| 2009/0227843 A1 | 9/2009 | Smith et al. |
| 2009/0292176 A1 | 11/2009 | Bonadio et al. |
| 2009/0326330 A1 | 12/2009 | Bonadio et al. |
| 2010/0063362 A1 | 3/2010 | Bonadio et al. |
| 2010/0063364 A1 | 3/2010 | Bonadio et al. |
| 2010/0081880 A1 | 4/2010 | Widenhouse et al. |
| 2010/0081881 A1 | 4/2010 | Murray et al. |
| 2010/0081995 A1 | 4/2010 | Widenhouse et al. |
| 2010/0100043 A1 | 4/2010 | Racenet |
| 2010/0113882 A1 | 5/2010 | Widenhouse et al. |
| 2010/0217087 A1 | 8/2010 | Bonadio et al. |
| 2010/0228091 A1 | 9/2010 | Widenhouse et al. |
| 2010/0228092 A1 | 9/2010 | Ortiz et al. |
| 2010/0228094 A1 | 9/2010 | Ortiz et al. |
| 2010/0240960 A1 | 9/2010 | Richard |
| 2010/0249523 A1 | 9/2010 | Spiegal et al. |
| 2010/0249524 A1 | 9/2010 | Ransden et al. |
| 2010/0249525 A1 | 9/2010 | Shelton, IV et al. |
| 2010/0249694 A1 | 9/2010 | Choi et al. |
| 2010/0261972 A1 | 10/2010 | Widenhouse et al. |
| 2010/0261975 A1 | 10/2010 | Huey et al. |
| 2010/0286484 A1 | 11/2010 | Stellon et al. |
| 2010/0298646 A1 | 11/2010 | Stellon et al. |
| 2010/0305407 A1 | 12/2010 | Farley |
| 2011/0021877 A1 | 1/2011 | Fortier et al. |
| 2011/0028891 A1 | 2/2011 | Okoniewski |
| 2011/0034935 A1 | 2/2011 | Kleyman |
| 2011/0034946 A1 | 2/2011 | Kleyman |
| 2011/0034947 A1 | 2/2011 | Kleyman |
| 2011/0071462 A1 | 3/2011 | Ewers et al. |
| 2011/0071463 A1 | 3/2011 | Ewers et al. |

FOREIGN PATENT DOCUMENTS

| | | |
|---|---|---|
| DE | 37 39 532 | 12/1988 |
| DE | 37 37 121 | 5/1989 |
| DE | 296 00 939 | 6/1996 |
| DE | 19828009 | 12/1999 |
| EP | 0113520 | 7/1984 |
| EP | 0142262 | 5/1985 |
| EP | 0 517 248 | 12/1992 |
| EP | 0537768 | 4/1993 |
| EP | 0 807 416 | 11/1997 |
| EP | 0 849 517 | 6/1998 |
| EP | 0950376 | 10/1999 |
| EP | 1118657 | 7/2001 |
| EP | 1 125 552 | 8/2001 |
| EP | 1312318 | 5/2003 |
| EP | 1407 715 | 4/2004 |
| EP | 1 609 429 | 12/2005 |
| EP | 2044889 | 4/2009 |
| EP | 2 340 792 | 7/2011 |
| FR | 1456623 | 9/1966 |
| GB | 1151993 | 5/1969 |
| GB | 1355611 | 6/1974 |
| GB | 1372491 | 10/1974 |
| GB | 1379772 | 1/1975 |
| GB | 1400808 | 7/1975 |
| GB | 1407023 | 9/1975 |
| GB | 1482857 | 8/1977 |
| GB | 1496696 | 12/1977 |
| GB | 2071502 | 9/1981 |
| GB | 2255019 | 10/1992 |
| GB | 2275420 | 8/1994 |
| GB | 2298906 | 9/1996 |
| IE | 930649 | 9/1993 |
| IE | 930650 | 9/1993 |
| IE | S940150 | 2/1994 |
| IE | S940613 | 8/1994 |
| IE | S940960 | 12/1994 |
| IE | S950055 | 1/1995 |
| IE | S950266 | 4/1995 |
| IE | S71634 | 2/1997 |
| IE | S75368 | 8/1997 |
| IE | S960196 | 8/1997 |
| IE | S970810 | 11/1997 |
| IE | 991010 | 7/2000 |
| IE | 990218 | 11/2000 |
| IE | 990219 | 11/2000 |
| IE | 990220 | 11/2000 |
| IE | 990660 | 2/2001 |
| IE | 990795 | 3/2001 |
| JP | 10-108868 | 4/1998 |
| JP | 11-290327 | 10/1999 |
| JP | 2001-61850 | 3/2001 |
| JP | 2002-28163 | 1/2002 |
| JP | 02003 235879 A | 8/2003 |
| JP | 2004-195037 | 7/2004 |
| JP | 2007-44395 | 2/2007 |
| RU | 1342485 | 1/1997 |
| WO | WO 86/06272 | 11/1986 |
| WO | WO 86/06316 | 11/1986 |
| WO | WO 92/11880 | 7/1992 |
| WO | WO 92/21292 | 12/1992 |
| WO | WO 93/05740 | 4/1993 |
| WO | WO 93/14801 | 8/1993 |
| WO | WO 94/04067 | 3/1994 |
| WO | WO 94/22357 | 10/1994 |
| WO | WO 95/05207 | 2/1995 |
| WO | WO 95/07056 | 3/1995 |
| WO | WO 95/22289 | 8/1995 |
| WO | WO 95/24864 | 9/1995 |

(56) References Cited

FOREIGN PATENT DOCUMENTS

| WO | WO 95/27445 | 10/1995 |
|---|---|---|
| WO | WO 95/27468 | 10/1995 |
| WO | WO 96/36283 | 11/1996 |
| WO | WO 97/11642 | 4/1997 |
| WO | WO 97/32514 | 9/1997 |
| WO | WO 97/32515 | 9/1997 |
| WO | WO 97/42889 | 11/1997 |
| WO | WO 98/19853 | 5/1998 |
| WO | WO 98/35614 | 8/1998 |
| WO | WO 98/48724 | 11/1998 |
| WO | WO 99/03416 | 1/1999 |
| WO | WO 99/15068 | 4/1999 |
| WO | WO 99/16368 | 4/1999 |
| WO | WO 99/22804 | 5/1999 |
| WO | WO 99/25268 | 5/1999 |
| WO | WO 99/29250 | 6/1999 |
| WO | WO 00/32116 | 6/2000 |
| WO | WO 00/32119 | 6/2000 |
| WO | WO 00/32120 | 6/2000 |
| WO | WO 00/35356 | 6/2000 |
| WO | WO 00/54675 | 9/2000 |
| WO | WO 00/54676 | 9/2000 |
| WO | WO 00/54677 | 9/2000 |
| WO | WO 01/08563 | 2/2001 |
| WO | WO 01/08581 | 2/2001 |
| WO | WO 01/26558 | 4/2001 |
| WO | WO 01/26559 | 4/2001 |
| WO | WO 01/45568 | 6/2001 |
| WO | WO 01/49363 | 7/2001 |
| WO | WO 01/91652 | 12/2001 |
| WO | WO 02/07611 | 1/2002 |
| WO | WO 02/17800 | 3/2002 |
| WO | WO 02/34108 | 5/2002 |
| WO | WO 03/011153 | 2/2003 |
| WO | WO 03/011551 | 2/2003 |
| WO | WO 03/026512 | 4/2003 |
| WO | WO 03/032819 | 4/2003 |
| WO | WO 03/034908 | 5/2003 |
| WO | WO 03/061480 | 7/2003 |
| WO | WO 03/077726 | 9/2003 |
| WO | WO 03/103548 | 12/2003 |
| WO | WO 2004/026153 | 4/2004 |
| WO | WO 2004/030547 | 4/2004 |
| WO | WO 2004/075730 | 9/2004 |
| WO | WO 2004/075741 | 9/2004 |
| WO | WO 2004/075930 | 9/2004 |
| WO | WO 2005/009257 | 2/2005 |
| WO | WO 2005/034766 | 4/2005 |
| WO | WO 2005/089661 | 9/2005 |
| WO | WO 2006/040748 | 4/2006 |
| WO | WO 2006/057982 | 6/2006 |
| WO | WO 2006/059318 | 6/2006 |
| WO | WO 2006/100658 | 9/2006 |
| WO | WO 2007/044849 | 4/2007 |
| WO | WO 2008/011358 | 1/2008 |
| WO | WO 2008/015566 | 2/2008 |
| WO | WO 2008/093313 | 8/2008 |
| WO | WO 2008/121294 | 10/2008 |
| WO | WO 2010/082722 | 7/2010 |
| WO | WO 2010/104259 | 9/2010 |

OTHER PUBLICATIONS

U.S. Appl. No. 10/381,220, filed Mar. 20, 2003; Title: Surgical Access Apparatus and Method, now U.S. Pat. No. 7,473,221 issued Jan. 6, 2009.

U.S. Appl. No. 10/436,522, filed May 13, 2003; Title: Laparoscopic Illumination Apparatus and Method, now U.S. Pat. No. 6,939,296 issued Sep. 6, 2005.

U.S. Appl. No. 10/399,209, filed Aug. 22, 2003; Title: Wound Retraction Apparatus and Method, now U.S. Pat. No. 6,958,037 issued Oct. 25, 2005.

U.S. Appl. No. 11/218,412, filed Sep. 1, 2005; Title: Wound Retraction Apparatus and Method, now U.S. Pat. No. 7,238,154 issued Jul. 3, 2007.

U.S. Appl. No. 10/399,057, filed Apr. 11, 2003; Title: Sealed Surgical Access Device, now U.S. Pat. No. 7,052,454 issued May 30, 2006.

U.S. Appl. No. 10/666,579, filed Sep. 17, 2003; Title: Surgical Instrument Access Device, now U.S. Pat. No. 7,163,510 issued Jan. 16, 2007.

U.S. Appl. No. 10/052,297, filed Jan. 18, 2002; Title: Hand Access Port Device, now U.S. Pat. No. 6,908,430 issued Jun. 21, 2005.

U.S. Appl. No. 08/015,765, filed Feb. 10, 1993; Title: Gas-Tight Seal Accomodating Surgical Instruments with a Wide Range of Diameters, now U.S. Pat. No. 5,407,433 issued Apr. 18, 1995.

U.S. Appl. No. 08/040,373, filed Mar. 30, 1993; Title: Gas-Tight Seal Accomodating Surgical Instruments with a Wide Range of Diameters, now U.S. Pat. No. 5,411,483 issued May 2, 1995.

U.S. Appl. No. 10/902,756, filed Jul. 29, 2004; Title: Hand Access Port Device, now abandoned.

U.S. Appl. No. 10/802,125, filed Mar. 15, 2004; Title: Surgical Guide Valve, now abandoned.

U.S. Appl. No. 10/516,198, filed Nov. 30, 2004; Title: Wound Retractor, now U.S. Pat. No. 7,650,887 issued Jan. 26, 2010.

U.S. Appl. No. 10/927,551, filed Aug. 25, 2004; Title: Surgical Access System, now abandoned.

U.S. Appl. No. 11/244,647, filed Oct. 5, 2005; Title: Surgical Access Apparatus and Method, now U.S. Pat. No. 7,481,765 issued Jan. 27, 2009.

U.S. Appl. No. 11/548,746, filed Oct. 12, 2006; Title: Method of Making a Hand Access Laparoscopic Device, now U.S. Pat. No. 7,749,415 issued Jul. 6, 2010.

U.S. Appl. No. 11/548,765, filed Oct. 12, 2006; Title: Split Hoop Wound Retractor, now U.S. Pat. No. 7,815,567 issued Oct. 26, 2010.

U.S. Appl. No. 11/548,767, filed Oct. 12, 2006; Title: Circular Surgical Retractor now U.S. Pat. No. 7,704,207 issued Apr. 27, 2010.

U.S. Appl. No. 11/548,781, filed Oct. 12, 2006; Title: Wound Retractor With Gel Cap, now U.S. Pat. No. 7,727,146 issued Jun. 1, 2010.

U.S. Appl. No. 11/548,955, filed Oct. 12, 2006; Title: Hand Access Laparoscopic Device, now U.S. Pat. No. 7,736,306 issued Jun. 15, 2010.

U.S. Appl. No. 11/755,305, filed May 30, 2007; Title: Wound Retraction Apparatus and Method, now U.S. Pat. No. 7,377,898 issued May 27, 2008.

U.S. Appl. No. 11/548,758, filed Oct. 12, 2006; Title: Split Hoop Wound Retractor with Gel Pad, now U.S. Pat. No. 7,909,760 issued Mar. 22, 2011.

U.S. Appl. No. 12/693,242, filed Jan. 1, 2010; Title: Wound Retractor, now U.S. Pat. No. 7,913,697 issued Mar. 29, 2011.

U.S. Appl. No. 12/768,328, filed Apr. 27, 2010; Title: Circular Surgical Retractor, now U.S. Pat. No. 7,892,172 issued Feb. 22, 2011.

U.S. Appl. No. 12/791,666, filed Jun. 1, 2010; Title: Wound Retractor with Gel Cap, now U.S. Pat. No. 7,883,461 issued Feb. 8, 2011.

U.S. Appl. No. 12/815,986, filed Jun. 15, 2010; Title: Hand Access Laparoscopic Device, now U.S. Pat. No. 7,878,974 issued Feb. 1, 2011.

U.S. Appl. No. 10/695,295, filed Oct. 28, 2003; Title: Surgical Gel Seal.

U.S. Appl. No. 11/132,741, filed May 18, 2005; Title: Gas-Tight Seal Accomodating Surgical Instruments with a Wide Range of Diameters.

U.S. Appl. No. 11/245,709, filed Oct. 7, 2005; Title: Surgical Access System.

U.S. Appl. No. 11/330,661, filed Jan. 12, 2006; Title: Sealed Surgical Access Device.

U.S. Appl. No. 11/564,409, filed Nov. 29, 2006; Title: Surgical Instrument Access Device.

U.S. Appl. No. 12/108,400, filed Apr. 23, 2008; Title: Wound Retraction Apparatus and Method.

U.S. Appl. No. 12/119,371, filed May 12, 2008; Title: Surgical Retractor with Gel Pad.

U.S. Appl. No. 12/119,414, filed May 12, 2008; Title: Surgical Retractor.

U.S. Appl. No. 12/358,080, filed Jan. 22, 2009; Title: Surgical Instrument Access Device.

U.S. Appl. No. 12/360,634, filed Jan. 27, 2009; Title: Surgical Access Apparatus and Method.

(56) References Cited

OTHER PUBLICATIONS

U.S. Appl. No. 12/360,710, filed Jan. 27, 2009; Title: Surgical Access Apparatus and Method.
U.S. Appl. No. 12/578,422, filed Oct. 13, 2009; Title: Single Port Access System.
U.S. Appl. No. 12/905,932, filed Oct. 15, 2010; Title: Split Hoop Wound Retractor.
U.S. Appl. No. 12/960,449, filed Dec. 3, 2010; Title: Surgical Access Apparatus and Method.
U.S. Appl. No. 12/960,458, filed Dec. 3, 2010; Title: Surgical Access Apparatus and Method.
U.S. Appl. No. 13/006,727, filed Jan. 14, 2011.
U.S. Appl. No. 13/008,728, filed Jan. 18, 2011.
U.S. Appl. No. 13/023,334, filed Feb. 8, 2011.
U.S. Appl. No. 13/031,892, filed Feb. 22, 2011.
U.S. Appl. No. 13/050,042, filed Mar. 17, 2011.
U.S. Appl. No. 10/446,365, filed May 28, 2003; Title: Screw-Type Seal with Inflatable Membrane.
U.S. Appl. No. 12/004,439, filed Dec. 20, 2007; Title: Skin Seal.
U.S. Appl. No. 12/004,441, filed Dec. 20, 2007; Title: Screw-Type Skin Seal with Inflatable Membrane.
U.S. Appl. No. 12/607,667, filed Oct. 28, 2009; Title: Screw-Type Skin Seal with Inflatable Membrane.
U.S. Appl. No. 10/965,217, filed Oct. 15, 2004; Title: Surgical Sealing Device.
U.S. Appl. No. 10/981,730, filed Nov. 5, 2004; Title: Surgical Sealing Device.
U.S. Appl. No. 11/246,909, filed Oct. 11, 2005; Title: Instrument Access Device.
U.S. Appl. No. 11/291,089, filed Dec. 1, 2005; Title: A Surgical Sealing Device.
U.S. Appl. No. 11/486,383, filed Jul. 14, 2006; Title: Wound Retractor.
U.S. Appl. No. 11/785,752, filed Apr. 19, 2007; Title: Instrument Access Device.
U.S. Appl. No. 12/244,024, filed Oct. 2, 2008; Title: Seal Anchor for Use in Surgical Procedures.
U.S. Appl. No. 12/578,832, filed Oct. 14, 2009; Title: Flexible Access Device for Use in Surgical Procedure.
U.S. Appl. No. 12/706,043, filed Feb. 16, 2010; Title: Flexible Port Seal.
U.S. Appl. No. 12/719,341, filed Mar. 8, 2010; Title: Foam Port and Introducer Assembly.
U.S. Appl. No. 10/895,546, filed Jul. 21, 2004; Title: Laparoscopic Instrument and Cannula Assembly and Related Surgical Method.
U.S. Appl. No. 10/913,565, filed Aug. 5, 2004; Title: Surgical Device With Tack-Free Gel and Method of Manufacture.
Dexterity Protractor Instruction Manual by Dexterity Surgical, Inc.
European Patent Office, European Search Report for European Application No. EP 10 18 4681, dated Nov. 22, 2010, entitled "Wound Retraction Apparatus and Method".
European Patent Office, European Search Report for European Application No. EP 10 18 4608, dated Nov. 22, 2010, entitled "Wound Retraction Apparatus and Method".
European Patent Office, European Search Report for European Application No. EP 10 18 4648, dated Nov. 22, 2010, entitled "Wound Retraction Apparatus and Method".
European Patent Office, European Search Report for European Application No. EP 10 18 4731, dated Nov. 22, 2010, entitled "Wound Retraction Apparatus and Method".
European Patent Office, European Search Report for European Application No. EP 10 18 4661, dated Nov. 22, 2010, entitled "Wound Retraction Apparatus and Method".
European Patent Office, European Search Report for European Application No. EP 10 18 4677, dated Nov. 22, 2010, entitled "Wound Retraction Apparatus and Method".
European Patent Office, European Search Report for European Application No. EP 10 18 9325, dated Dec. 14, 2010, entitled "Split Hoop Wound Retractor".
European Patent Office, European Search Report for European Application No. EP 10 18 9327, dated Dec. 14, 2010, entitled "Split Hoop Wound Retractor".
European Patent Office, European Search Report for European Application No. EP 10 18 9328, dated Dec. 15, 2010, entitled "Split Hoop Wound Retractor".
European Patent Office, European Search Report for European Application No. EP 04 00 2888, dated Sep. 10, 2004, entitled "Hand Access Port Device".
European Patent Office, European Search Report for European Application No. EP 04 00 2889, dated Sep. 13, 2004, entitled "Hand Access Port Device".
European Patent Office, International Search Report and the Written Opinion of the International Searching Authority for International Application No. PCT/US2006/040154, mailed Jan. 30, 2007.
European Patent Office, International Search Report and the Written Opinion of the International Searching Authority for International Application No. PCT/US2006/040073, mailed Jan. 26, 2007.
European Patent Office, International Search Report and the Written Opinion of the International Searching Authority for International Application No. PCT/US2006/039905, mailed Jan. 17, 2007.
European Patent Office, International Search Report and the Written Opinion of the International Searching Authority for International Application No. PCT/US2006/039883, mailed Jan. 31, 2007.
European Patent Office, International Search Report and the Written Opinion of the International Searching Authority for International Application No. PCT/US2006/039800, mailed Apr. 16, 2007.
European Patent Office, International Search Report and the Written Opinion of the International Searching Authority for International Application No. PCT/US2006/039799, mailed Mar. 27, 2007.
European Patent Office, Supplementary European Search Report for European Patent Application No. 08755322, dated Apr. 18, 2012.
European Patent Office, Supplementary European Search Report for European Patent Application No. 08755336, dated Jun. 15, 2012.
European Patent Office, International Search Report and Written Opinion for International Application No. PCT/US2012/037111, titled Wound Retractor, mailed Aug. 30, 2012.
European Search Report for corresponding EP 08253236 date of mailing is Feb. 10, 2009 (6 pages).
Horigame, et al., Silicone Rumen Cannula with a Soft Cylindrical Part and a Hard Flange, Journal of Dairy Science, Nov. 1989, vol. 72, No. 11, pp. 3230-3232.
Horigame, et al., Technical Note: Development of Duodoenal Cannula for Sheep, Journal of Animal Science, Apr. 1992, vol. 70, Issue 4, pp. 1216-1219.
International Searching Authority/US, International Search Report and the Written Opinion of the International Searching Authority for International Application No. PCT/US04/05484.
International Searching Authority/US, International Search Report and the Written Opinion of the International Searching Authority for International Application No. PCT/US01/29682.
McSweeney, Cannulation of the Rumen in Cattle and Buffaloes, Australian Veterinary Journal, Aug. 1989, vol. 66, No. 8, pp. 266-268.
Neil Sheehan, Supplemental Expert Report of Neil Sheehan, Re: U.S. Pat. No. 5,741,298, United States District Court for the Central District of California, Civil Action No. SACV 03-1322 JVS, Aug. 9, 2005.
Office Action in co-pending U.S. Appl. No. 12/360,634, dated Jan. 24, 2011 in 12 pages.
Office Action in co-pending U.S. Appl. No. 12/360,710, dated Jan. 24, 2011 in 12 pages.
Technical Note: Development of Duodenal Cannula for Sheep, Faculty of Agriculture and School of Medicine Tohokju University, Sendai 981, Japan.
The International Bureau of WIPO, International Preliminary Report on Patentability, dated Aug. 29, 2006, for International Application No. PCT/US2004/028250.
The International Bureau of WIPO, International Preliminary Report on Patentability, dated Apr. 16, 2008, for International Application No. PCT/US2006/039799.
The International Bureau of WIPO, International Preliminary Report on Patentability for International Application No. PCT/US2006/039800 dated Apr. 16, 2008.

(56) References Cited

OTHER PUBLICATIONS

Yamazaki, et al., Diurnal Changes in the Composition of Abomasal Digesta in Fasted and Fed Sheep, The Tohoki Journal of Agricultural Research, Mar. 1987, vol. 37, No. 3-4, pp. 49-58.

Kagaya, Laparascopic cholecystecomy via two ports, using the "Twin-Port" system, J. Hepatobiliary Pancreat Surg (2001) 8:76-80.

International Search Report and Written Opinion in PCT/IE2005/000113 mailed on Feb. 22, 2006.

International Search Report and Written Opinion in PCT/IE2007/000050 mailed on Aug. 13, 2007.

Declaration of John R. Brustad dated Dec. 10, 2009, submitted in U.S. Appl. No. 11/548,955, including Appendices A-D regarding product sales brochures and production drawings from 2001 and 2005.

The International Searching Authority, The International Search Report and Written Opinion of the International Searching Authority for International Application No. PCT/US08/63445, mailed Sep. 29, 2008.

The International Searching Authority, The International Search Report and Written Opinion of the International Searching Authority for International Application No. PCT/US08/063463 mailed Sep. 10, 2008.

The International Bureau of WIPO, International Preliminary Report on Patentability for International Application No. PCT/US2008/063463, dated Nov. 17, 2009, entitled "Surgical Retractor".

The International Bureau of WIPO, International Preliminary Report on Patentability for International Application No. PCT/US08/63445, issued Nov. 17, 2009, entitled "Surgical Retractor with Gel Pad".

International Searching Authority—US, International Search Report and Written Opinion of the International Searching Authority for International Application No. PCT/US04/25511, mailed Nov. 7, 2007.

International Bureau of WIPO, International Report on Patentability for International Application No. PCT/US04/25511, mailed Dec. 6, 2007.

International Search Report and Written Opinion of the International Searching Authority for PCT application No. PCT/US01/29682.

European Patent Office, European Search Report for European Patent No. 11172709.5, dated Aug. 16, 2011.

European Patent Office, European Search Report for European Patent No. 11172706.1, dated Aug. 16, 2011.

Harold W. Harrower, M.D. Isolation of Incisions into Body Cavities, The American Journal of Surgery, p. 824-826.

The International Bureau of WIPO, International Preliminary Report on Patentability for International Application No. PCT/US2012/037111, titled "Wound Retractor" dated Nov. 12, 2013.

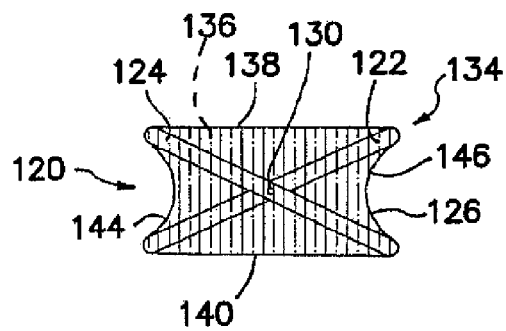
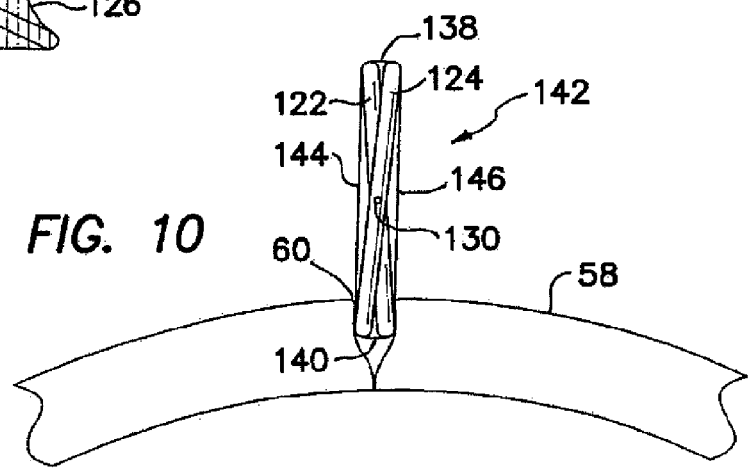
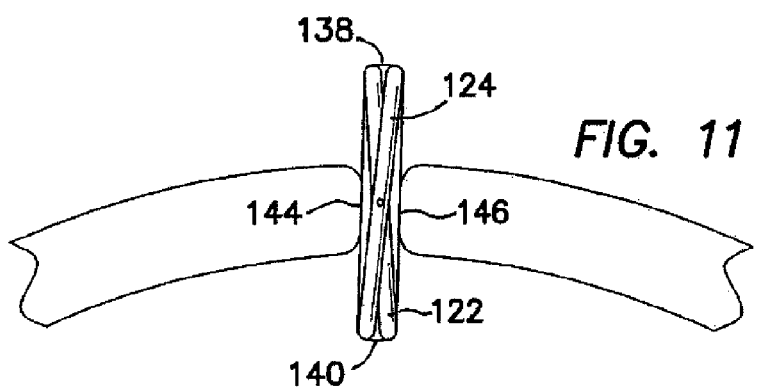
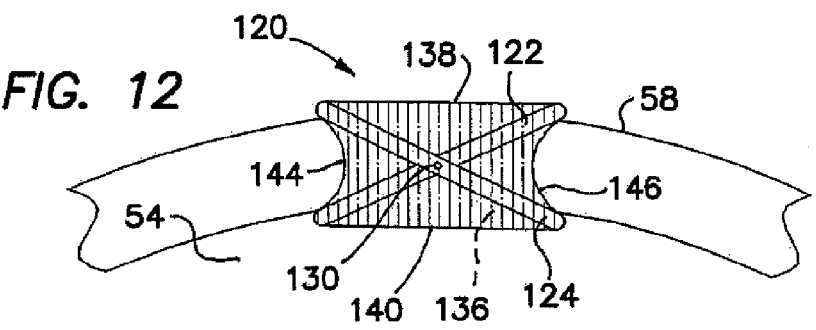

WOUND RETRACTOR

CROSS-REFERENCE TO RELATED APPLICATIONS

This application is a division of U.S. patent application Ser. No. 13/467,825, filed on May 9, 2012, which claims benefit of U.S. Provisional Patent Application No. 61/484,362, filed on May 10, 2011, the disclosures of which are hereby incorporated by reference as if set forth in full herein.

BACKGROUND

Tissue retraction during surgery is commonly accomplished by placing opposed instruments within an incision and spreading the incision open with the instruments. Another method includes the use of circumferentially expandable plates or segments that expand to enlarge an incision. The enlarged incision is held open by the expanded device. Additionally, the retraction device may be configured to isolate the incised walls so that they are not contaminated as a surgery proceeds.

Other retraction devices according to the prior art include a pair of opposed, flexible rings where a first ring is placed on one side of a body wall, a second ring is placed on the opposite side of the body wall, and a thin film of waterproof material is stretched between the two rings. Some configurations of these devices can be difficult to place and may require the use of an assistant to attain proper tensioning.

There remains a need for an easily placed and easily adjustable retraction device for maintaining retraction of an incision during a surgical procedure.

SUMMARY

The present invention provides a device that may be inserted into a surgical incision in a first condition and subsequently expanded or reshaped to retract the incision. The invention also contemplates the use of an impermeable film or sheet associated with the tissue-contacting portions to provide a fluid tight and gastight barrier that is sized and configured to prevent transfer of biological components.

A retraction device of the present invention is adapted to retract an incision in a body wall. The retraction device includes a first, outer ring, a second, inner ring, a first hinge that couples the first to the second ring, and a second hinge that couples the first ring to the second ring. The first and second hinges are positioned along a common axis and substantially opposite each other on the circumference of the first and second rings. The retraction device also includes a tubular sheath that is coupled around the circumference of the first ring and around the circumference of the second ring. In a first, concentric state, the first and second rings are substantially concentric with each other, while in a second, angular state, the first and second rings are rotated about the axis and form an angle between the planes of the first and second rings. The retraction device also includes means for maintaining the retraction device in the second, angular state. The sheath is substantially cylindrical when the first and second rings are in the second, angular state.

In one aspect, the sheath is substantially not tensioned when the retraction device is in the first, concentric state. In the first, concentric state, the retraction device may be further streamlined by compressing the first and second rings along the axis between the first and second hinges to facilitate insertion of the retraction device into the incision in the body wall. The maintaining means may include a ratchet mechanism positioned proximate at least one of the first and second hinges. The ratchet mechanism may be positioned proximate each of the first and second hinges. In another aspect, the maintaining means may include a valve structure mounted onto the retraction device external the body wall. The sheath may be formed from an elastomeric material. In another aspect, the sheath may be formed from a non-distensible material.

In another embodiment of the invention, the retraction device includes a first ring, a second ring, a first hinge that couples the first ring to the second ring, a second hinge that couples the first ring to the second ring, and a stretchable, tubular sheath that is coupled to each of the first and second rings. The first and second hinges are positioned along a common axis and substantially opposite each other on the circumference of the first and second rings. In a first, relaxed state in which an angle is formed between the planes of the first and second rings, the sheath is substantially relaxed and forms a substantially through lumen between a proximal end and a distal end of the retraction device. In a second, tensioned state in which the first and second rings are rotated toward each other across the proximal and distal opening planes, the first and second rings are substantially concentric with the sheath being tensioned between the first and second rings. When the retraction device is in the second, tensioned state, release of the tension upon the elastomeric sheath allows the retraction device to assume the first, relaxed state.

In one aspect, when the retraction device is in the second, tensioned state, the lumen of the sheath is reduced and substantially occluded and the retraction device is substantially flat. In the second, tensioned state, the retraction device may be streamlined further by compressing the first and second rings along the axis between the first and second hinges to facilitate insertion of the retraction device into the incision in the body wall.

In another embodiment of the invention, the retraction device includes a distal continuous ring, a first half ring, a second half ring, a first hinge that couples the distal ring, the first half ring and the second half ring together, a second hinge that couples the distal ring, the first half ring and the second half ring together, and a circumferential, elastomeric sheath that is coupled between the distal ring and the first and second half rings. The first and second hinges are positioned along a common axis and substantially opposite each other on the circumference of the distal ring. In a first, neutral condition, the first half ring is positioned on a first side of the axis, proximal the distal ring, and the second half ring is positioned on a second, opposite side of the axis proximal the distal ring. In a second, tensioned condition, the first half ring is rotated about the first and second hinges in a first direction to a position on the second side of the axis and proximal the distal ring, thereby placing the portion of the sheath that is coupled between the distal ring and the first half ring in tension. The second half ring is rotated about the first and second hinges in a second, opposite direction to a position on the first side of the axis and proximal the distal ring, thereby placing the portion of the sheath that is coupled between the distal ring and the second half ring in tension.

The first and second half rings may be rotated further about the axis until they are substantially concentric with the distal ring. In the second, tensioned condition, the retraction device may be further streamlined by compressing the distal ring and the first and second half rings along the axis between the first and second hinges to facilitate insertion of the retraction device into the incision in the body wall. The sheath may be further coupled between the first and second half rings. At least one of the first and second half rings may be positioned along an outer surface of the distal ring. Alternatively, at least one of the first and second half rings may be positioned along an inner surface of the distal ring. First end portions of each of the first half ring and the second half ring may overlap and second end portions of each of the first half ring and the second half ring may overlap. In one aspect, the first end portion of the first half ring is positioned between the distal ring and the first end portion of the second half ring, the second end portion of the first half ring is positioned between the distal ring and the second end portion of the second half ring, and the first and second half rings are adapted to rotate past each other as the first and second half rings are rotated about the first and second hinges. The distal ring may be adapted to abut against an inner surface of the body wall.

In another embodiment of the invention, the retraction device includes a first, distal retention ring, a second, proximal retention ring, a circumferential, tubular sheath that is coupled to the first and second retention rings, a plurality of tensioning straps, and a proximal lock ring. The sheath includes a lumen. Each of the plurality of straps is coupled to the distal retention ring and extends proximally through the lumen of the sheath and the proximal retention ring. The lock ring is sized and configured to capture the straps between an inner surface of the proximal retention ring and an outer surface of the lock ring. The lock ring is adapted to be positioned within a lumen of the proximal retention ring with the straps exiting between the proximal retention ring and the lock ring. The straps are adapted to be pulled proximally to achieve appropriate tension and subsequent retraction of the incision. The lock ring responds to the tension of the straps by wedging against the inner surface of the proximal retention ring and substantially preventing the straps from slipping distally between the lock ring and the proximal retention ring.

At least one of the inner surface of the proximal retention ring and the outer surface of the lock ring may be beveled. Each of the plurality of straps may be formed of a strong, thin, non-elastic material. Release of tension of the plurality of straps may be accomplished by pulling at least one of the tensioned straps proximally slightly to release the lock ring from the proximal ring and removing the lock ring.

In another embodiment of the invention, the retraction device includes a proximal retention ring and a plurality of shapeable extending elements that are coupled to the proximal retention ring and extend distally from the proximal retention ring. The extending elements are configured to transition from a first, low-profile, insertion condition to a second, expanded, high-profile retention condition in which distal ends of the extending elements extend radially outwardly.

The retraction device may also include a circumferential sheath positioned within a lumen of the retraction device. The proximal retention ring may be adapted to abut against an outer surface of the body wall. The extending elements may be made of strips of sheet metal having an axially semicircular cross section with each of the extending elements oriented with the outer curve of the semicircular cross section positioned radially outwardly and being adapted to transform to a second, curved, high-profile condition when bent inwardly on the outer semicircular surface. The extending elements may be made of spring steel. In one aspect, the extending elements may be made of a shape-memory material such that at a first temperature, the extending elements are in a first, substantially straight condition, and at a second, higher temperature, the extending elements transform to a second, curved condition where the distal ends of the extending elements extend radially outwardly. The shape-memory material may include nickel-titanium alloy.

In one aspect, the retraction device may also include a plurality of pull wires with each of the pull wires being coupled to a distal portion of a respective extending element and configured to deflect the respective extending element radially outwardly when the pull wire is pulled proximally. The retraction device may also include a circumferential sheath positioned within a lumen of the retraction device. The proximal retention ring may be adapted to abut against an outer surface of the body wall. The extending elements may be made of spring steel. The pull wires may be deployed either collectively or individually. In one aspect, the retraction device a pull wire retainer may be positioned along the length of the outer surface of each of the extending elements and each of the pull wires may traverse through a respective pull wire retainer. Each pull wire retainer may include a tube with the respective pull wire traversing through the tube. In another aspect, each pull wire retainer may include at least one eyelet with the pull wires traversing through the respective eyelets. The at least one eyelet may include a plurality of eyelets that is longitudinally aligned along the length of the respective extending element with the pull wires traversing through the respective plurality of eyelets.

In another embodiment of the invention, the retraction device may include an outer ring having a substantially annular shape with an adjustable circumference, a substantially tubular structure extending distally from the outer ring, and means for adjusting the circumference of the outer ring. The outer ring is divided into a plurality of curved ring segments. Each of the curved ring segments includes a first, proximal side, a second, distal side, a first end about the circumference of the outer ring, and a second end about the circumference of the outer ring. The substantially tubular structure is divided into a plurality of elongate tube segments. Each of the tube segments is coupled to a respective curved ring segment and extends distally from the respective curved ring segment. The diameter of the outer ring is increased by moving the curved ring segments further apart and is decreased by moving the curved ring segments closer together.

Each of the tube segments of the tubular structure may extend circumferentially between the first end and second end of the respective curved ring segment to which it is coupled such that there is substantially no overlap between adjacent tube segments. In another aspect, each of the tube segments may extend circumferentially beyond at least one of the first and second ends of the respective curved ring segment to which it is coupled such that adjacent tube segments overlap. The profile of each of the tube segments may substantially follow the curve of the respective curved ring segment to which it is coupled. The curved ring segments may be flexible to maintain a substantially circumferential shape of the outer ring as the diameter of the outer ring is adjusted. Each of the tube segments may be substantially flexible so as to follow changes of the curve of the respective curved ring segment to which it is coupled. The means for adjusting the circumference of the outer ring may include a ratcheting mechanism that is adapted to couple adjacent curved ring segments of the outer ring together to form the annular shape of the outer ring. In one aspect, the retraction device includes an inner ring that is coupled to a distal end of the tubular structure. The inner ring is substantially opposite to the outer ring.

In one aspect, the ratcheting mechanism may include a groove in the proximal surface of each of the curved ring segments, a plurality of ratchet teeth positioned in each of the grooves, an elongate protuberance extending from the second end of each of the curved ring segments, and at least one ratchet tooth positioned on each of the protuberances. The grooves may substantially follow the curve of the respective curved ring segment and be open to the first end of the respective curved ring segment. The groove forms a first, outer curved surface and a second, inner curved surface. The protuberances may be adapted to mate with the groove in an adjacent curved ring segment. The at least one ratchet tooth on the protuberance is adapted to interact with the ratchet teeth in the groove of the respective adjacent curved ring segment. The first end of each of the curved ring segments may be positioned adjacent the second end of an adjacent curved ring segment and the elongate protuberance of each curved ring segment may be inserted into the groove of the other adjacent curved ring segment such that the at least one ratchet tooth on the elongate protuberance interacts with the ratchet teeth in the groove. The ratchet teeth may be positioned on the first, outer curved surface of the groove of the respective curved ring segment or on the second, inner curved surface of the groove of the respective curved ring segment. Alternatively, the ratchet teeth may be positioned on a distal surface of the groove of the respective curved ring segment. In one aspect, the retraction device also includes a retention channel that is positioned in each of the grooves in at least one of the first, outer curved surface and second, inner curved surface of the respective groove. A lip is positioned on each of the elongate protuberances. The lip extends longitudinally along the length of the respective protuberance and is adapted to interact with the retention channel in the groove of the respective adjacent curved ring segment.

In another embodiment of the invention, the retraction device includes a tubular sheath having a first, proximal end and a second, distal end, a first, folded condition in which the sheath has a first circumference, and a second, unfolded condition in which the sheath has a second circumference that is larger than the first circumference. The sheath is sufficiently long to fit completely through the body wall. In the first, folded condition, the sheath has undulations about its circumference. The sheath is biased toward the second, unfolded condition. The sheath may be compressed to the first, folded condition such that when the force holding the sheath in the first, folded condition is removed, the sheath opens to the second, unfolded condition.

The sheath may be formed from a malleable, substantially circular member. In one aspect, the retraction device also includes means to compress the sheath into the first, folded condition. The compressing means may include a drawstring that is threaded through the undulations of the sheath. The sheath may be adapted to be compressed into the first, folded condition when the drawstring is pulled radially away from the sheath and to expand to the second, unfolded condition when the drawstring is subsequently released.

In another embodiment of the invention, the retraction device includes a first, outer ring, a second, inner ring, a substantially cylindrical sleeve that is coupled to the first and second rings, a first biasing member that is associated with the first, outer ring, and a second biasing member that is associated with the second, inner ring. The first biasing member biases the first ring radially outwardly and the second biasing member biases the second ring radially outwardly. The first and second biasing members place the cylindrical sleeve in tension to retract the incision.

The first and second biasing members may each include a spring-like core that positioned within the first and second outer ring, respectively. The cylindrical sleeve may include radial folds that allow the cylindrical sleeve to transition between a first, axially compressed state and a second, axially extended state. In the first, axially compressed state, the retraction device may be further compressed radially at opposing points along the inner and outer rings to transform the retraction device into a low profile, elongate, substantially oval shape to facilitate insertion into the incision.

In another embodiment of the invention, the retraction includes a first, outer ring a second, inner ring, and a substantially cylindrical sleeve coupled to the first and second rings. The outer ring is sized and configured to remain outside a body cavity. The inner ring is flexible and is adapted to be compressed radially at opposing points along its circumference to transform the inner ring into an elongate, oval shape to facilitate insertion into the incision and into a body cavity. The cylindrical sleeve is configured to be tensioned between the first ring and the second ring. The first ring includes a substantially hollow, inflatable structure. The retraction device is adapted to increase tension on the sleeve to retract the incision by inflating the first ring when the first ring is positioned outside the body and the second ring is positioned in the body cavity. In one aspect, the cylindrical sleeve includes radial folds that allow the cylindrical sleeve to transition between a first, axially compressed state and a second, axially extended state.

These and other features of the invention will become more apparent with a discussion of the various embodiments in reference to the associated drawings.

BRIEF DESCRIPTION OF THE DRAWINGS

FIG. 9 is a side view of a cross-ring retraction device in a non-tensioned condition prior to insertion into an incision in a body wall;

FIG. 10 is a side view of the cross-ring retraction device of FIG. 9 in a fully tensioned, folded, low profile condition suitable for insertion through the incision in the body wall;

FIG. 11 is a side view of the insertion step of the cross-ring retraction device of FIG. 9 through the incision in the body wall;

FIG. 12 is a side view of the deployment step of the cross-ring retraction device of FIG. 9 where the cross-ring retraction device is allowed to assume a preset tension to retract the incision in the body wall;

DESCRIPTION

Figure 1:
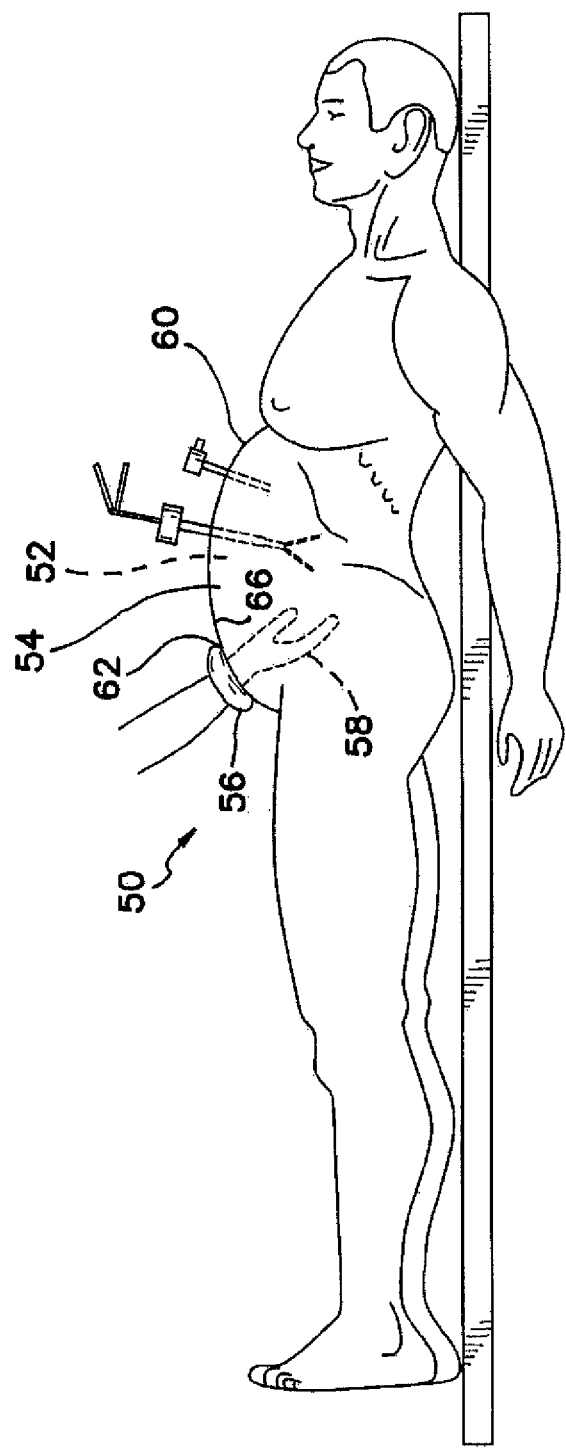
FIG. 1 is a side view of a hand assisted laparoscopic procedure where a retraction device is in place.
Figure 2:
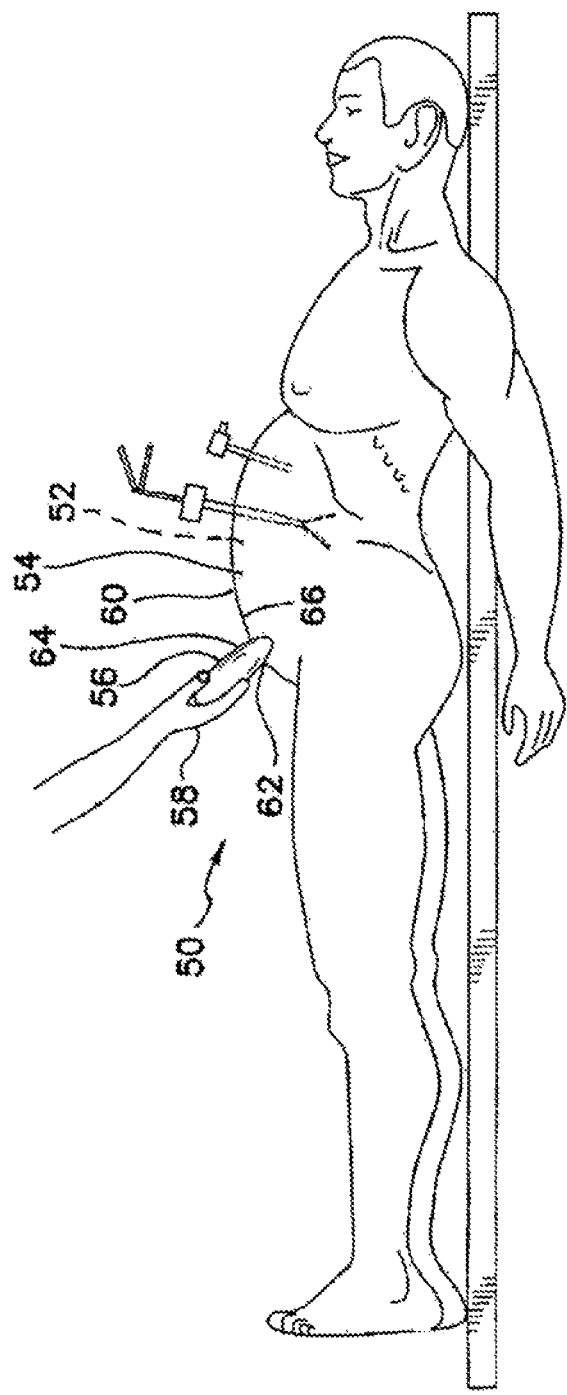
FIG. 2 is a side view of a hand assisted laparoscopic procedure showing the placement of a retraction device.
Figure 3:
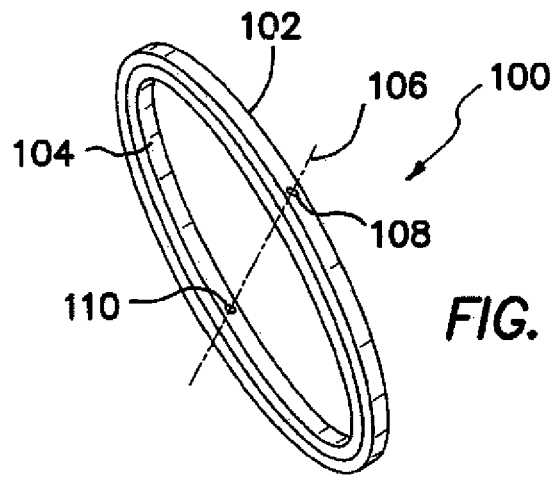
FIG. 3 is a perspective view of a frame for a hinged retraction device in a folded, low profile, insertion condition.
Figure 4:
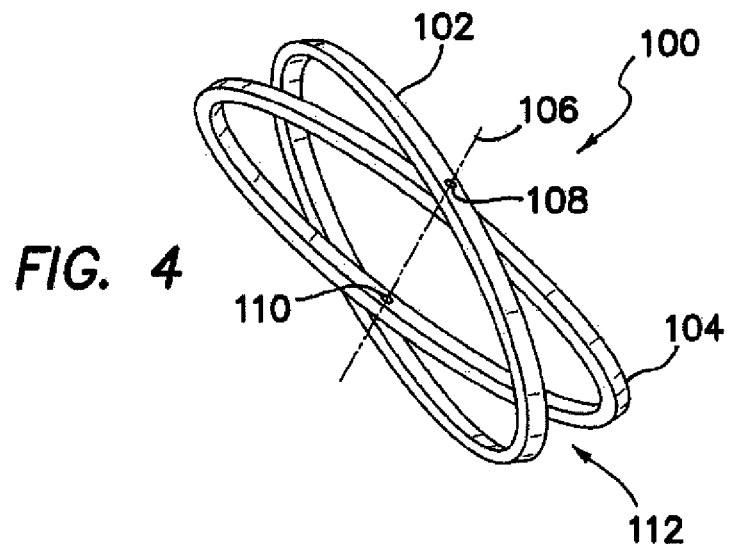
FIG. 4 is a perspective view of the frame for the hinged retraction device of FIG. 3 in a low profile, mid-deployment condition.
Figure 5:
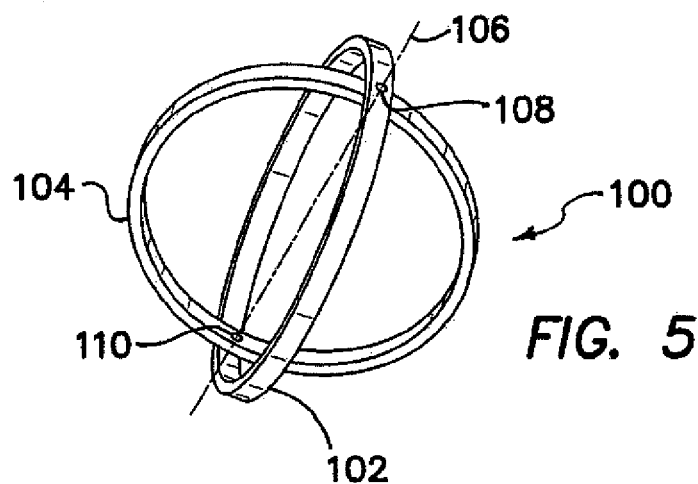
FIG. 5 is a perspective view of the frame for the hinged retraction device of FIG. 3 in an open condition.
Figure 6:
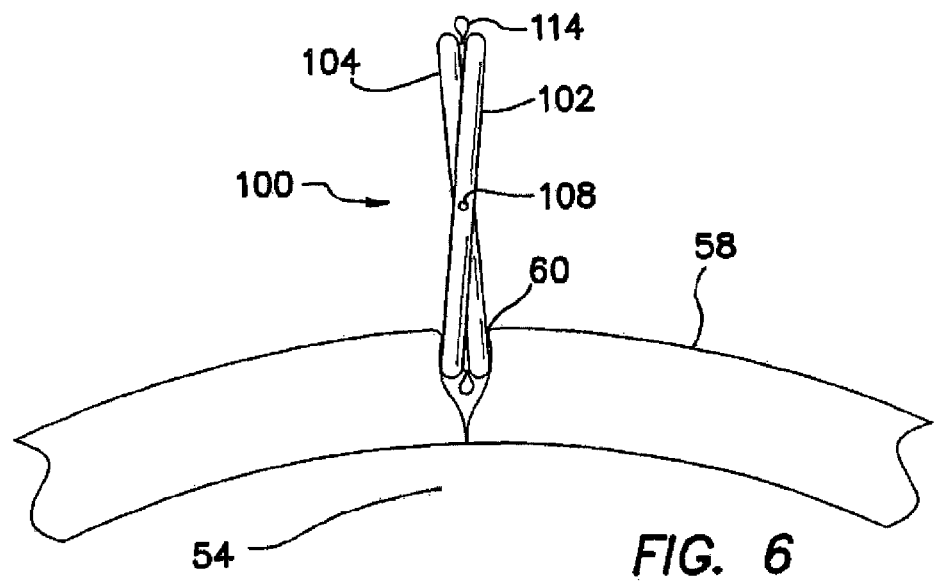
FIG. 6 is a side view of a hinged retraction device in a folded, low profile condition suitable for insertion into an incision.
Figure 7:
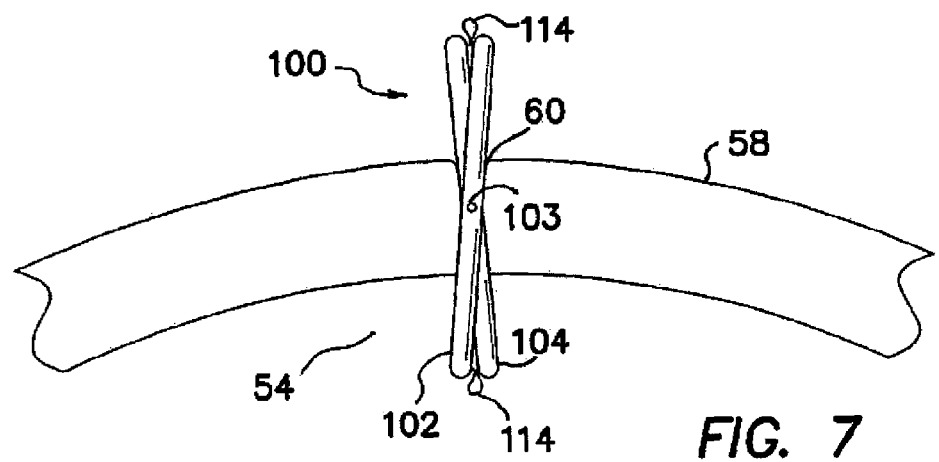
FIG. 7 is a side view of the hinged retraction device of FIG. 6 in a folded, low profile condition fully inserted into the incision and into a body cavity.
Figure 8:
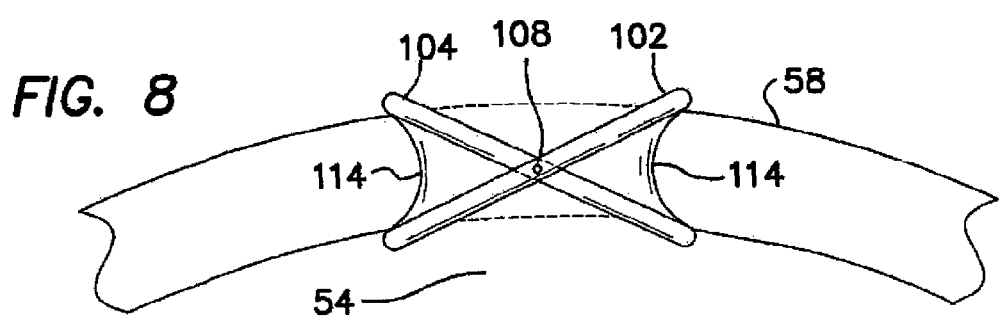
FIG. 8 is a side view of the hinged retraction device of FIG. 6 fully inserted into the incision and fully deployed within the body cavity to retract the incision.
Figure 14:
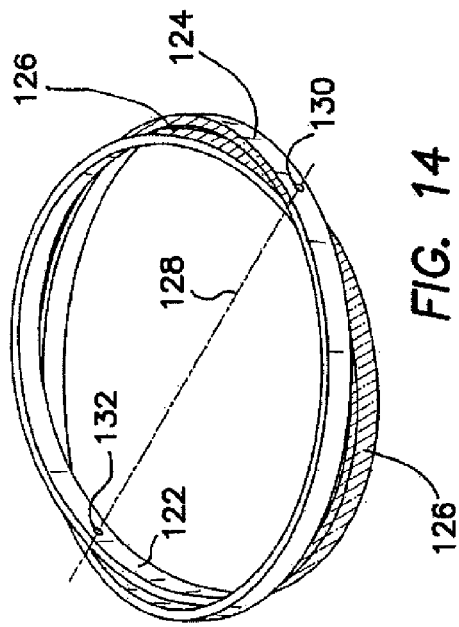
FIG. 14 is a perspective view of the cross-ring retraction device of FIG. 9 as it is prepared for tensioning prior to insertion through the incision in the body wall.
Figure 16:
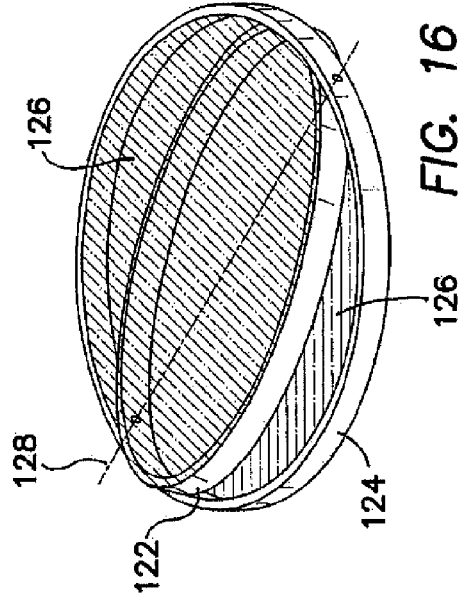
FIG. 16 is a perspective view of the cross-ring retraction device of FIG. 9 partially tensioned prior to insertion through the incision in the body wall.
Figure 13:
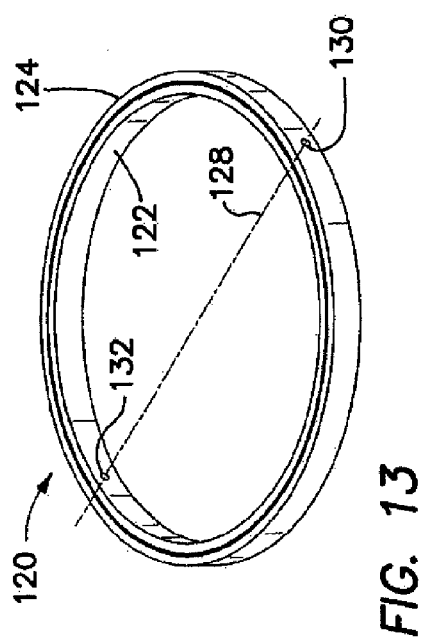
FIG. 13 is a perspective view of the cross-ring retraction device of FIG. 9 in a stored condition.
Figure 15:
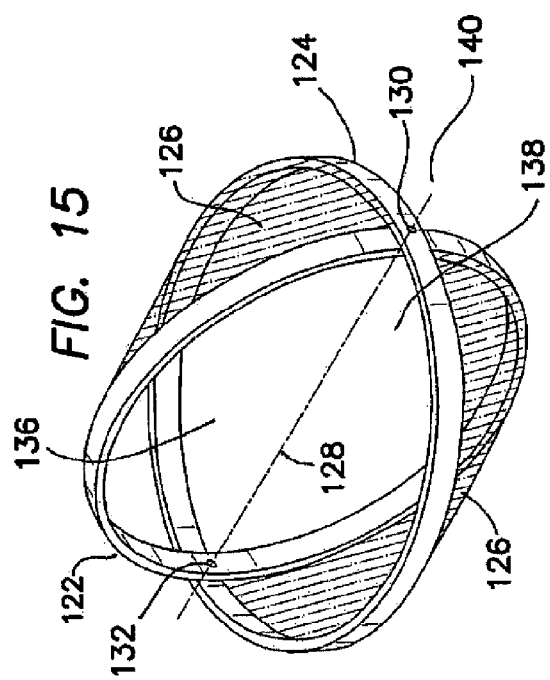
FIG. 15 is a perspective view of the cross-ring retraction device of FIG. 9 partially tensioned prior to insertion through the incision in the body wall.
Figure 17:
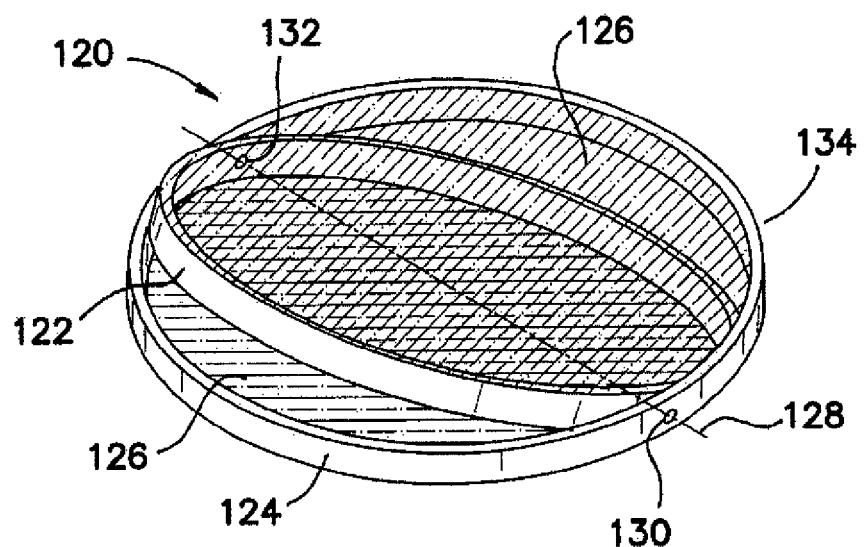
FIG. 17 is a perspective view of the cross-ring retraction device of FIG. 9 partially tensioned prior to insertion through the incision in the body wall prior to the step of reducing the insertion profile by compressing the cross-ring along the folding axis into an oval shape.
Figure 18:
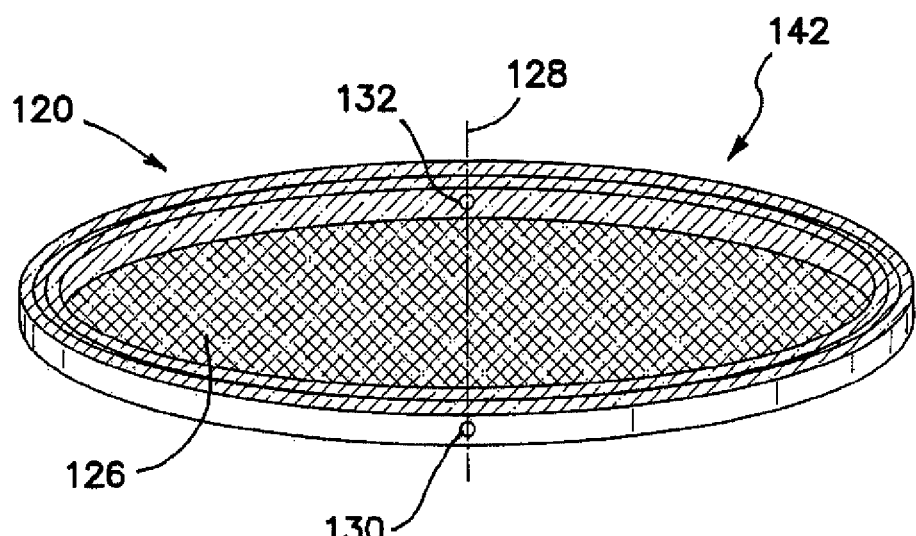
FIG. 18 is a perspective view of the cross-ring retraction device of FIG. 9 fully tensioned prior to insertion through the incision in the body wall and further prepared by compressing the cross-ring along the folding axis into an oval shape.

With reference to the drawings, FIGS. 1 and 2 depict a hand assisted laparoscopic surgery 50 where an abdominal cavity 52 is created within an abdominal region 54 of a body by the introduction of a pressurized gas. A retraction device 56 is shown having a human hand 58 therethrough. To deploy the retraction device 56 within a patient's abdominal wall 60, a surgical incision 62 is made through the abdominal wall and the retraction device is inserted and subsequently deployed to retract and enlarge the incision. The retraction device 56 may include a first, outer retention member, a second, inner retention member, and a membrane or sleeve coupled between the first retention member and the second retention member. The retraction device 56 may be shapeable 64 to facilitate placement through a small incision 62. The retraction device 56 may be held by a hand in a low profile shape and condition 64 as it is inserted through the incision 62 and subsequently released so that the first, outer retention member and the second, inner retention member stretch the membrane between an outer surface of the body wall 60 and an inner surface 66 of the body wall.

Referring to FIGS. 3-8, a retraction device 100 is shown having a first, outer ring 102 and a second, inner ring 104 that are substantially concentric with each other. The first and second rings 102, 104 may be semi-rigid and hinged along a common axis 106 that forms a first hinge 108 and a second hinge 110 that couple the first ring 102 and the second ring 104 together with the hinges being positioned substantially opposite each other on the circumference of the first and second rings. The retraction device 100 may transition from a first, concentric state (FIG. 3) to a second, angular state (FIGS. 4, 5 and 8) 112 where the first and second rings 102, 104 are rotated about the axis 106 and form an angle between the planes of the first and second rings. The form of the retraction device 100 generally resembles a collapsible gyroscope. A gastight tubular membrane or sheath 114 (FIGS. 6-8) is coupled around the circumference of the first ring 102 and around the circumference of the second ring 104 such that when the first and second rings are in the second, angular state, the sheath is substantially cylindrical.

The first and second rings 102, 104 are first compressed together to form a substantially concentric structure (FIGS. 6 and 7) where the wall of the membrane or sheath 114 is either not tensioned or only lightly tensioned. The compressed, concentric structure may be further streamlined by compressing the first and second rings 102, 104 along the axis between the first and second hinges 108, 110 to facilitate insertion of the retraction device 100 into the incision 62 in the body wall 60. The further streamlining along the axis significantly elongates the retraction device 100 so that it can slide through a small incision 62. Once the retraction device 100 has been inserted into the incision 62 to about the midpoint of the device, with the axis between the first and second hinges 108, 110 being positioned substantially parallel to the abdominal wall 60 and parallel to the incision, the retraction device is unfolded and deployed so that the membrane or sleeve 114 is stretched within the incision 62. As the two rings 102, 104 of the device 100 are rotated about the axis 106 between the first and second hinges 108, 110, the membrane or sleeve 114 places retracting tension upon the tissue surrounding the membrane or sleeve. The first ring 102 and the second ring 104 now traverse the incision 62 and the extending portions of the rings abut the outer surface of the body wall 60 and the inner surface 66 of the body wall. This arrangement maintains the retraction device 100 in place within the incision 62 and also retracts and enlarges the incision.

The retraction device 100 includes means for maintaining the retraction device in the second, angular state 105. Such maintaining means may include a ratchet mechanism that is positioned proximate at least one of the first and second hinges 108, 110. The ratchet mechanism may be positioned proximate each of the first and second hinges 108, 110. Alternatively, the maintaining means may include a valve structure mounted onto the retraction device external the body wall 60. Other means for maintaining the retraction device 100 in the open, deployed condition include any suitable mechanical means that is well known in the art.

The first and second rings 102, 104 may be made from a semi-rigid plastic material having sufficient strength to normally form a circle when no external forces are applied. Alternatively, the first and second rings 102, 104 may include a metal or plastic reinforcing member placed within an elastomeric hollow or tubular structure forming the first and second rings. The rings 102, 104 may also be made of a spring-like metal structure where the rings are formed from a flat metal spring or a round metal spring. Additionally, the rings 102, 104 may be formed of a shapeable or malleable metallic material or composite. Alternatively, one of the first and second rings 102, 104 may be made from a material having a first characteristic and the other one of the first and second rings may be made from a second material having a second characteristic. More particularly, the first ring 102 may be made of a more rigid material than the second ring 104. For example, the first ring 102 may be made of a semi-rigid metal or plastic and the second ring 104 may be made of a plastic or other material less rigid than the material of which the first ring is made. When the first and second rings 102, 104 are compressed together (FIG. 3), the circumference of the second ring is collapsed to fit within the circumference of the first ring.

The membrane or sheath 114 may be formed from an elastomeric material or a thin, non-distensible material. The elastomeric materials may include silicone, polyisoprene, latex, vinyl and polyurethane. The non-elastic materials may include polyester, Mylar, polyethylene, and the like. These materials may be reinforced with a fabric or woven material to increase strength and durability.

Referring to FIGS. 9 through 18, a cross-ring wound retraction device 120 includes first and second retracting portions or rings 122, 124 and a gastight, stretchable, tubular membrane, or sheath 126, that may be tensioned between the retracting portions. The first and second retracting portions 122, 124 are substantially concentric. The first and second retracting portions 122, 124 may be hinged along a common axis 128, thereby forming first and second hinges 130, 132 that couple the first and second retracting portions together. The hinges 130, 132 are positioned substantially opposite each other on the circumference of the first and second retracting portions 122, 124. The sheath 126 is coupled to each of the first and second retracting portions 122, 124.

The cross-ring retraction device 120 may be supplied in a first, relaxed state 134 (FIG. 9) where the circumferential elastomeric sheath 126 is substantially non-tensioned or relaxed. In the first, relaxed state 134, an angle is formed between the planes of the first and second rings 122, 124 and there is a substantial through lumen 136 between the proximal end 138 and the distal end 140 of the retraction device 120. To place the retraction device 120 in a second, tensioned state 142, the profile of the retraction device may be reduced and deformed to facilitate placement through a small surgical incision 62 by rotating the retracting portions 122, 124 toward each other across the proximal 138 and distal 140 opening planes such that the first and second rings become substantially concentric. The elastomeric sheath 126 is subsequently stretched longitudinally between the proximal end 138 and the distal end 140, thereby placing the sheath in tension, with the opening of the lumen 136 being reduced and substantially occluded and the retraction device becoming substantially flat (see FIGS. 13-18). Additionally, once the retraction device 120 has been thus flattened, it may be streamlined further into an oval shape (FIG. 18) by compressing the rings 122, 124 along the axis 128 of the first and second hinges 130, 132. The retraction device 120, in the flattened, streamlined condition (FIG. 18) will fit through a much smaller incision 62 than is the case when the device is at rest 134. The retraction device 120 may be urged through a surgical defect, such as an incision 62 (FIGS. 1 and 2), in a body wall 60 and subsequently allowed to assume the first relaxed state 134 in response to the release of the tension upon the elastomeric sheath 126. The lumen 136, including the proximal and distal openings 138, 140 thereof, will open as the retraction device 120 assumes an open, deployed condition (FIG. 12). The elastomeric sheath 126 forms a continuous, gastight barrier 144, 146 between the lumen 136 of the retraction device 120 and the tissue of the retracted incision or defect 62.

The elastomeric material of which the sheath 126 is made may be chosen to provide a range of retracting forces. For instance, a light weight, thin-walled, more elastic material yields a light retraction force in comparison to a thick-walled, less elastic material. Various diameters of retraction rings 122, 124 may be combined with various qualities of elastomeric material to yield retraction devices that accommodate a wide range of body wall conditions or types. The present invention also contemplates the use of rigid or semi-rigid plastic or spring metal for the construction of the first and second retracting portions or rings 122, 124.

Referring to FIGS. 19 through 25, a retraction device 150 may include a distal continuous ring 152, a first half ring 154 hinged to the distal continuous ring, a second half ring 156 hinged to the distal continuous ring, and a gastight, circumferential elastomeric sheath 158 coupled between the distal ring and the first and second half rings. The sheath 158 may also be coupled directly between the first and second half rings 154, 156.

Figure 19:
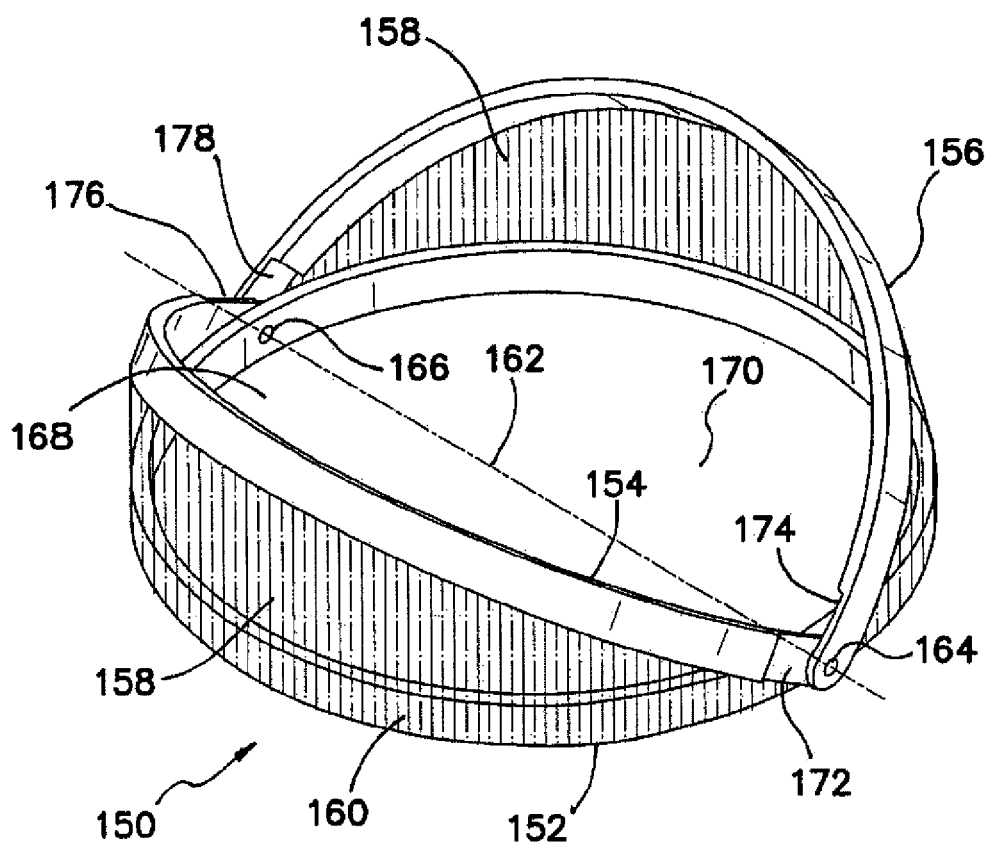
FIG. 19 is a perspective view of a cross-ring retraction device that comprises a first rigid ring and a plurality of folding portions.

One or both of the first and second half rings 154, 156 may be positioned along the outer surface 160 of the distal continuous ring 152 and hinged along a common axis 162, thereby forming a first hinge 164 and a second hinge 166 that couple the first and second half rings to each other and to the distal continuous ring with the hinges being positioned substantially opposite each other on the circumference of the distal continuous ring (FIG. 19). Alternatively, one or both of the first and second half rings 154, 156 may be positioned along the inner surface of the distal continuous ring 152 (FIGS. 20-25). In a first, neutral condition (FIG. 19), the first half ring 154 is positioned on a first side 168 of the axis 162, proximal the distal continuous ring 152, and the second half ring 156 is positioned on a second, opposite side 170 of the axis proximal the distal continuous ring.

A first end portion 172 of the first half ring 154 and a first end portion 174 of the second half ring 156 overlap each other and a second end portion 176 of the first half ring and a second end portion 178 of the second half ring overlap each other. The first and second end portions 172, 176 of the first half ring 154 may be positioned between the distal continuous ring 152 and the first and second end portions 174, 178 of the second half ring 156, respectively, so that the first and second half rings may rotate past each other. The retraction device may transition to a second, tensioned condition (FIG. 21) by folding the first half ring 154 and the second half ring 156 flat and in alignment with the distal continuous ring 152. In the second, tensioned condition, the first half ring, the second half ring and the distal continuous ring may be substantially concentric.

Figure 20:
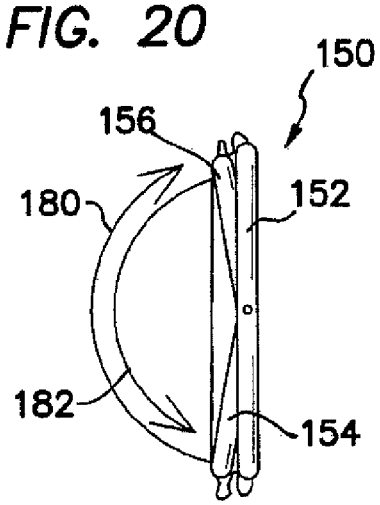
FIG. 20 is a side view of the cross-ring retraction device of FIG. 19 in a stored condition, prior to tensioning.
Figure 21:
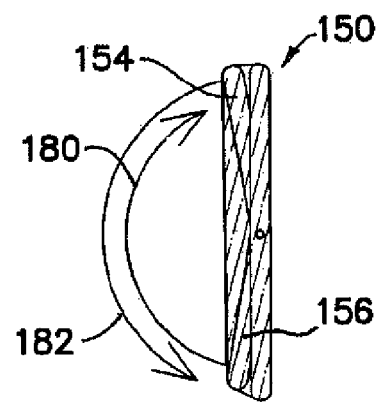
FIG. 21 is a side view of the cross-ring retraction device of FIG. 19 prepared for use by rotating the folding members.
Figure 22:
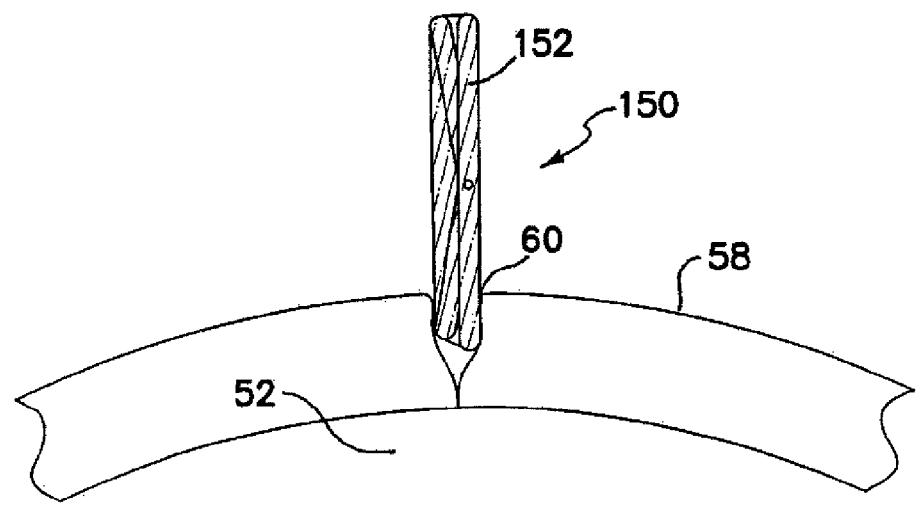
FIG. 22 is a side view of the cross-ring retraction device of FIG. 19 as it is inserted into the incision in the body wall.
Figure 23:
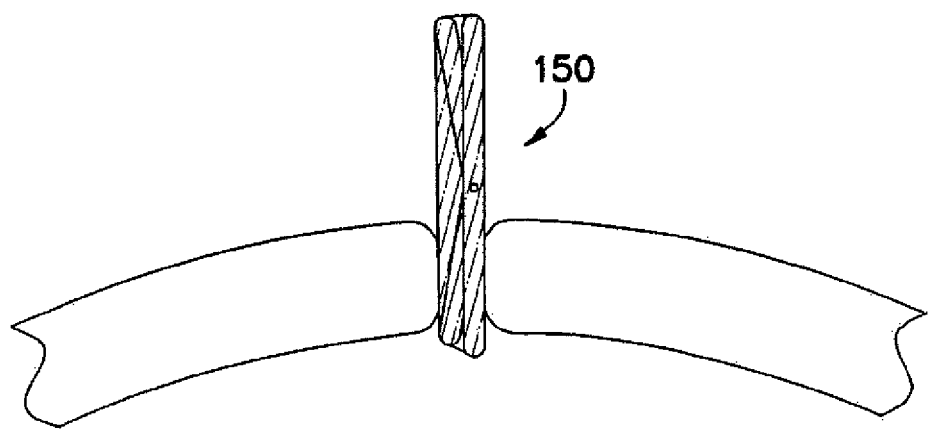
FIG. 23 is a side view of the cross-ring retraction device of FIG. 19 as it is further inserted into the incision in the body wall on its way to being fully inserted through the incision and completely into the body cavity.
Figure 24:
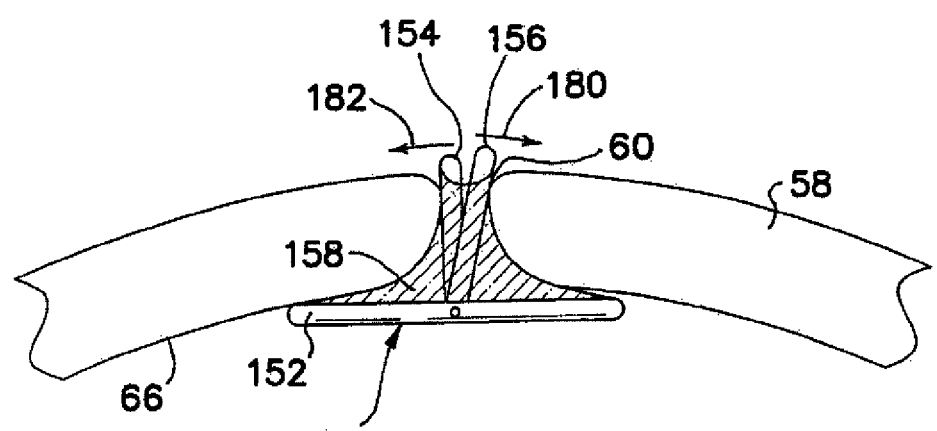
FIG. 24 is a side view of the cross-ring retraction device of FIG. 19 rotated into the deployed position with the rigid ring against the inner surface of the body wall and the folding portions rotated partially back toward the stored condition and extending through the incision in the body wall.
Figure 25:
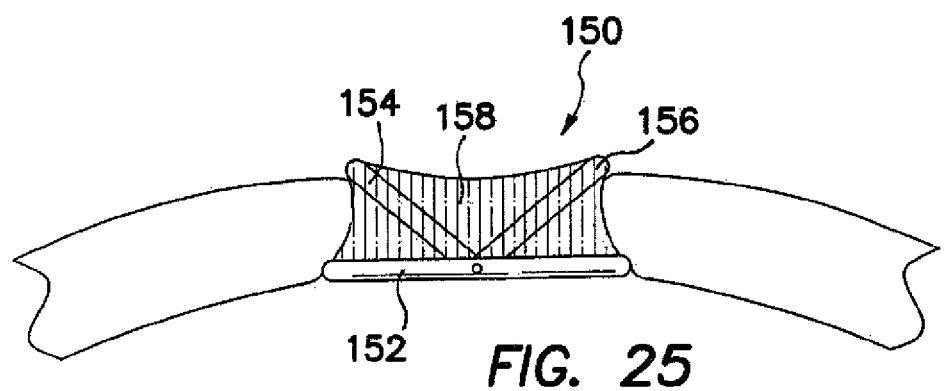
FIG. 25 is a side view of the cross-ring retraction device of FIG. 19 as it is fully inserted through a body wall and allowed to assume a deployed condition as it attempts to assume the stored condition.

Preparing the retraction device 150 for insertion into an incision 62 in a body wall 60 includes transitioning the retraction device from the first, neutral condition to a second, tensioned condition. The transition from the first, neutral condition (FIG. 19) to the second, tensioned condition (FIG. 21) includes the first half ring 154 being rotated about the hinges 164, 166 in a first direction 180 to a position on the second side 170 of the axis 162 and proximal the distal continuous ring 152, thereby placing the portion of the sheath 158 that is coupled between the distal ring and the first half ring in tension (FIGS. 20 and 21). The second half ring 156 is rotated about the hinges 164, 166 in a second, opposite direction 182 to a position on the first side 168 of the axis 162 and proximal the distal continuous ring 152, thereby placing the portion of the sheath 158 that is coupled between the distal ring and the second half ring in tension (FIGS. 20 and 21). The first and second half rings 154, 156 may be rotated about the hinges 164, 166 further until they are substantially concentric with the distal continuous ring 152. The retraction device 150 may be further streamlined by compressing the distal continuous ring 152 and the first and second half rings 154, 156 along the axis 162 between the first and second hinges 164, 166, thereby elongating the retraction device 150 to facilitate insertion of the retraction device into the incision 62 more easily (FIGS. 22 and 23).

The retraction device 150 is inserted completely through the incision 62 and completely into the body cavity 52. With the retraction device 150 positioned completely within the body cavity 52, the second half ring 156 is rotated back in the first direction 180 and the first half ring 154 is rotated back in the second direction 182 until the first and second half rings are substantially perpendicular to the distal continuous ring 152, substantially parallel to each other and proximal to the distal continuous ring (see FIG. 24). The first and second half ring 154, 156 are pulled proximally through the incision 62 until the distal continuous ring 152 abuts against the inner surface 66 of the body wall 60 and the first and second half ring are partially protruding from the incision. The first and second half ring 154, 156 are released and allowed to assume a nearly neutral condition (FIG. 25), thereby circumferentially retracting the incision 62.

Figure 26:
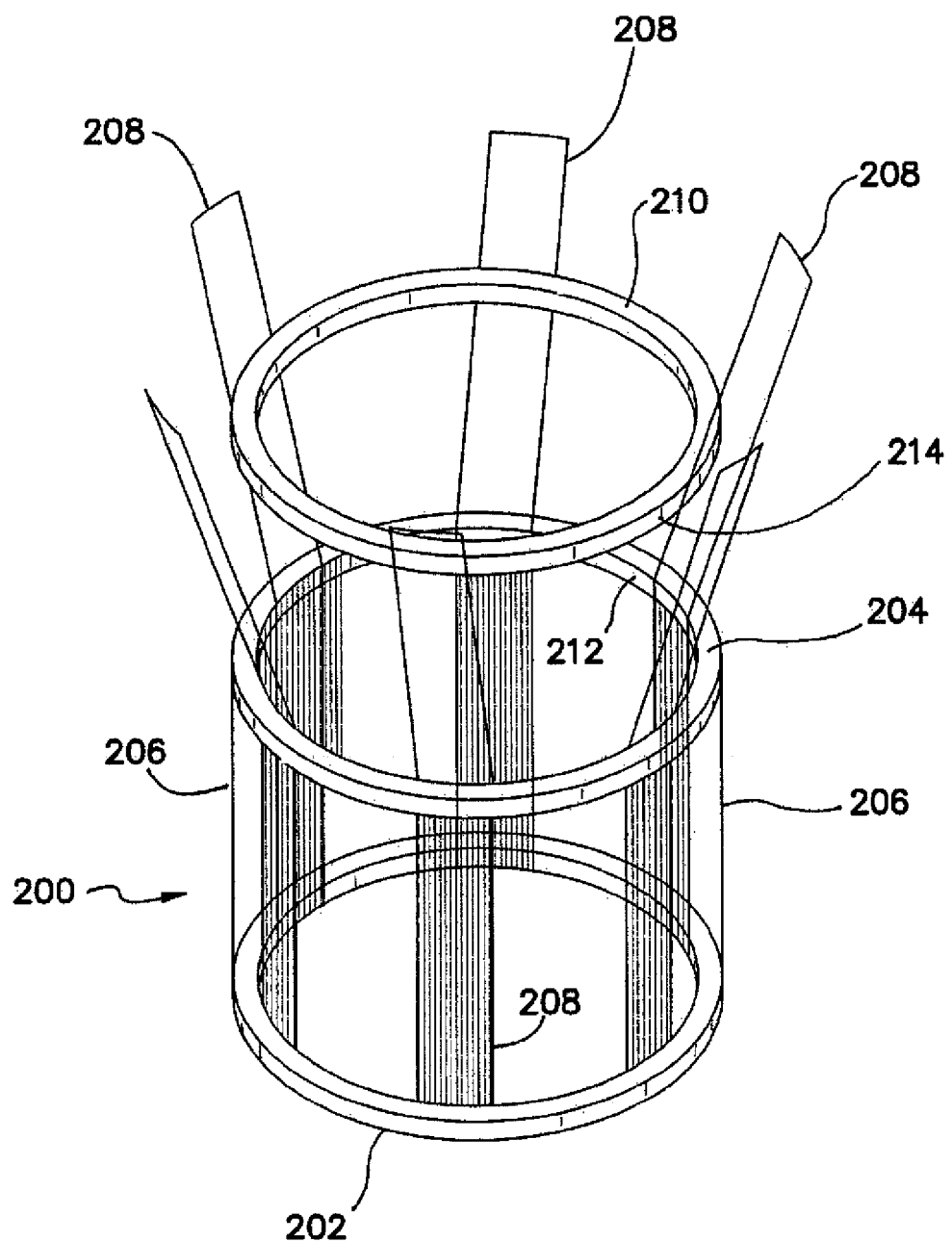
FIG. 26 is a perspective view of a wound retraction device having a plurality of straps for providing tension between a first retention ring and a second retention ring.

With reference to FIG. 26, a retraction device 200 is shown having a first, distal retention ring 202, a second, proximal retention ring 204, a circumferential, tubular sheath 206 coupled to the first and second retention rings, a plurality of tensioning straps 208 and a proximal lock ring 210. The distal retention ring 202 may be made from a shapeable or malleable material that may be deformed for easy insertion through a small body wall incision and subsequently allowed to assume a generally circular condition. The proximal retention ring 204 may be made from a material more rigid than the distal retention ring 202. Each of the plurality of straps 208 is coupled to the distal retention ring 202 and extends proximally through a lumen of the sheath 206 and the proximal retention ring 204. The proximal lock ring 210 is sized and configured to capture the straps 208 between an inner surface 212 of the proximal retention ring 204 and an outer surface 214 of the lock ring 210. At least one of the inner surface 212 of the proximal retention ring 204 and the outer surface 214 of the lock ring 210 may be beveled. The invention contemplates the use of a strong, thin, non-elastic material, such as a fabric, for the construction of the straps 208.

In use, the distal retention ring 202 is deformed and inserted into a body cavity 52 through an incision 62 in a body wall 60. The proximal retention ring 204 is allowed to rest upon the outer surface of the body wall 60. The lock ring 210 is placed within a lumen of the proximal retention ring 204 with the straps 208 exiting between the proximal retention ring and the lock ring. The straps 208 may be pulled proximally to achieve the appropriate tension and subsequent retraction of the incision. The lock ring 210 responds to the tension of the straps 208 by wedging against the inner surface 212 of the proximal retention ring 204 and substantially preventing the straps from slipping distally between the lock ring and the proximal retention ring. Removal of the retraction device 200 is accomplished by pulling at least one of the straps 208 proximally slightly to release the lock ring 210 from the proximal ring 204 and removing the lock ring to release the tension on the straps. With the tension of the straps 208 removed, the distal ring 202 may be removed from the body cavity 52 through the incision.

Figure 27:
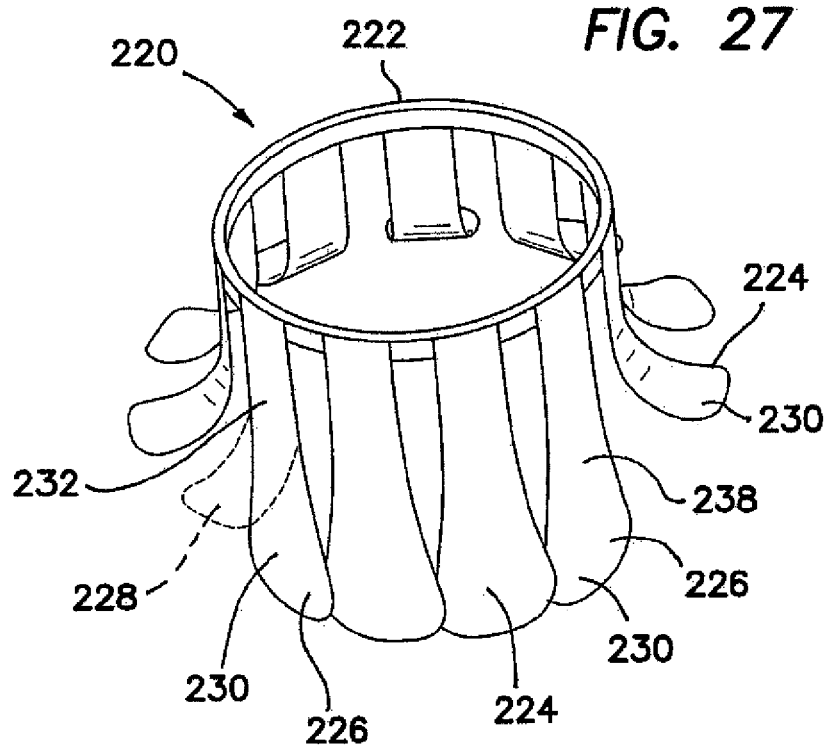
FIG. 27 is a perspective view of a ring-shaped retraction device having a plurality of shapeable extensions in a first condition.
Figure 28:
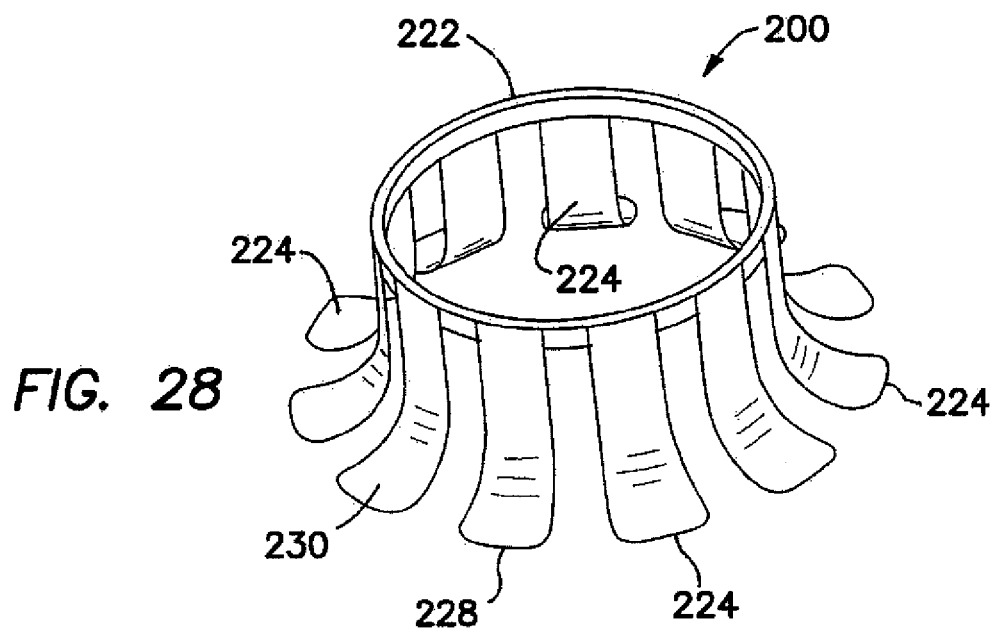
FIG. 28 is a perspective view of the ring-shaped retraction device of FIG. 27 having the plurality of shapeable extensions in a second, deployed condition.
Figure 29:
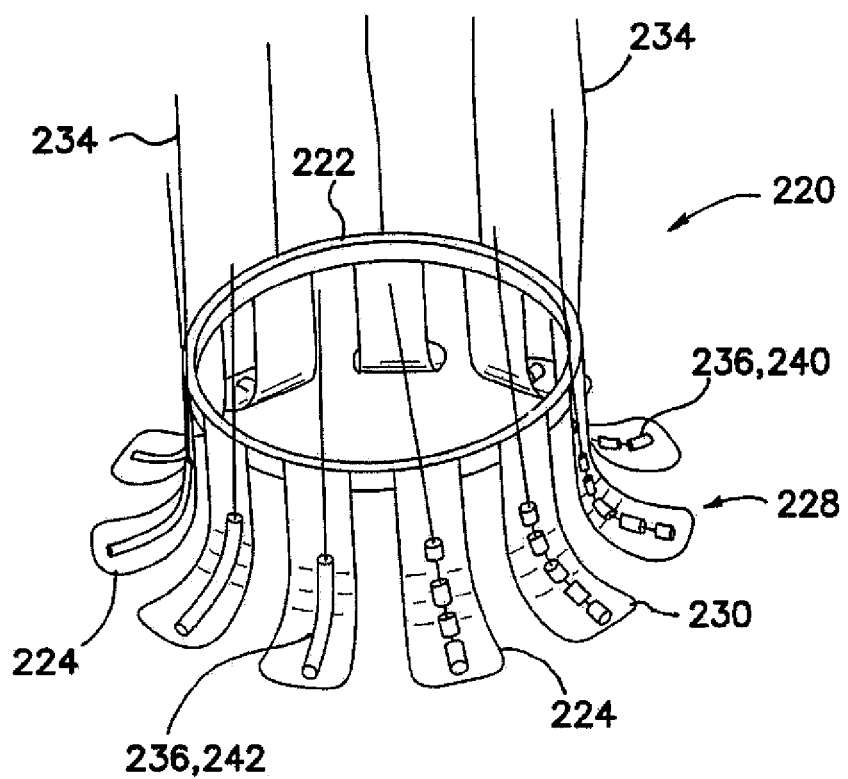
FIG. 29 is a perspective view of a ring-shaped retraction device, similar to the ring-shaped retraction device of FIG. 27, including pull wires for changing the shape of the extensions.

Referring to FIGS. 27-29, a wound retraction device 220 includes a proximal retention ring 222 and a plurality of shapeable, distally extending, retraction elements 224 coupled to the proximal retention ring and extending distally therefrom. The extending, retraction elements 224 are configured to transition from a first, low-profile, insertion condition 226 (FIG. 27) to a second, expanded, high-profile retention condition 228 in which distal ends of the extending elements extend radially outwardly (FIG. 28). The retention ring 222 may be sized and configured to hold the extending elements 224 in a generally perpendicular position to the plane of the retention ring. Alternatively, the extending elements 224 may extend radially inwardly to facilitate insertion or the retraction device 220 into the incision 62. The extending elements 224 may be malleable so as to be shaped into a retracted state within an incision or they may be sized and configured to snap between a first, inwardly disposed condition to the second, outwardly disposed condition 228 in a détente relationship. A circumferential sheath may be associated with the retraction device 220 and positioned either between the extending elements 224 and adjacent tissue or within a lumen of the retraction device as a separate component.

In use, the extending elements 224 are inserted into a surgical incision 62 (FIGS. 1 and 2) in a body wall 60 and advanced distally until the proximal retention ring 222 is substantially abutted against an outer surface of the body wall. A surgeon may then insert his hand distally through the retention ring 222 and bend a distal portion 230 of each of the extending elements 224 radially outwardly such that the distal portions of the extending elements are placed against an inner surface 66 of the body wall 60.

The extending elements 224 may be made of thin strips of sheet metal, such as spring steel, having a cupped or axially semicircular cross section resembling a steel tape measure or a slat of a venetian blind. Each of the extending elements 224 is oriented with the outer curve 232 of the semicircular cross section positioned radially outwardly. The extending elements 224 easily exist in the first, straight, insertion condition 226. However, once bent inwardly on the outer semicircular surface 232, the extensions transform to the second, curved, high-profile condition 228 for retention in the incision.

The extensions 224 may be made of a shape-memory material, such as nickel-titanium alloy. At a first temperature, the extending elements 224 made of nickel-titanium alloy may be in a first, substantially straight condition 226, and when placed in an environment having a second, higher temperature, the extensions transform to a second, curved condition 228 with the distal ends of the extending elements extending radially outwardly. For example, the device 220 may be held in a relatively cold environment, such as in ice water, and subsequently inserted into a warm environment where the temperature is higher, such as in a live body. The shape of nickel-titanium alloy extending elements 224 changes according to a preset condition.

Referring to FIG. 29, the wound retraction device 220 may include a plurality of pull wires 234 with each pull wire corresponding with a respective extending element 224. Each of the pull wires 234 is coupled to a distal portion 230 of a respective extending element 224 and configured such that when the pull wire is pulled proximally, the distal portion of the respective extending element deflects radially outwardly. Each pull wire 234 forces the distal portion 230 of the respective extending element 224 to exhibit a shape that is determined by the tension of the pull wire. The pull wires 234 may be deployed collectively or individually to bend the extending elements 224. Each of the pull wires 234 may traverse through a pull wire retainer 236 that is positioned along the length of the outer surface 238 of a respective extending element 224. Each pull wire retainer 236 may include at least one eyelet 240, tube 242 or other similarly functioning device. The pull wire retainers 236 function to limit the distance that the pull wires 234 deviate from the outer surface 238 of the extending elements 224 when the pull wires are pulled proximally to deflect the distal portions 230 of the extending elements. The pull wire retainers 236 may be longitudinally aligned along the length of the outer surface 238 of the extending element 224.

Figure 30:
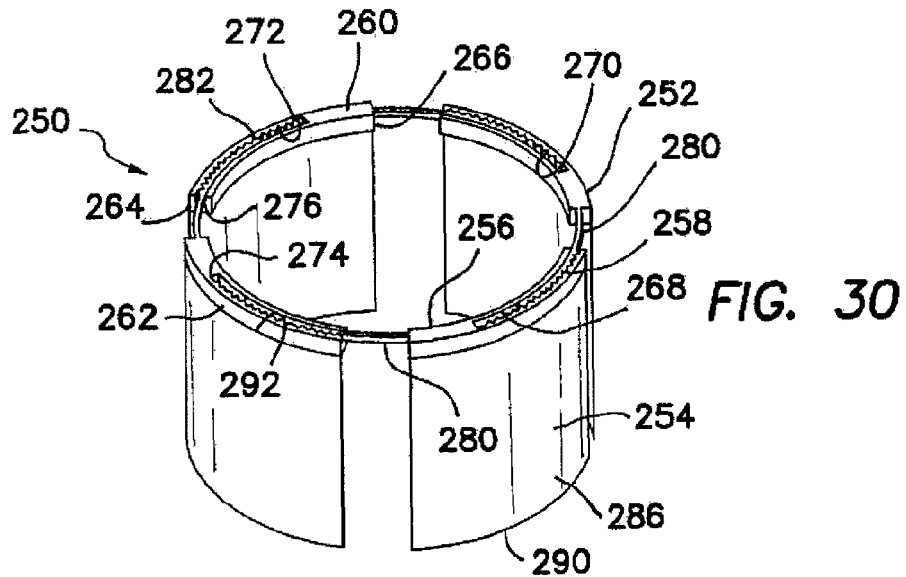
FIG. 30 is a perspective view of a ring-shaped retraction device having a plurality of adjustable retracting portions that allow adjustment of the ring diameter.
Figure 31:
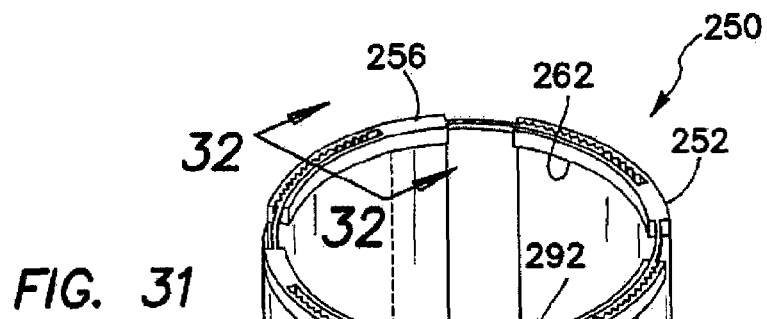
FIG. 31 is a perspective view of a ring-shaped retraction device having a plurality of adjustable retracting portions that allow adjustment of the ring diameter and having overlapping extensions.
Figure 32:
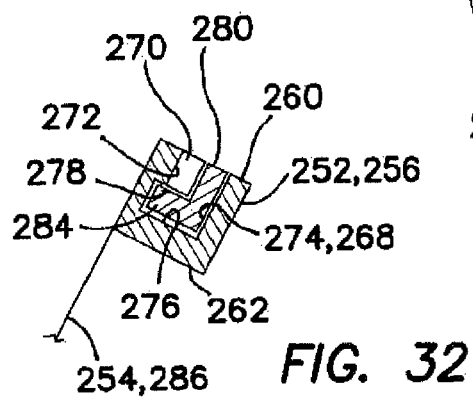
FIG. 32 is a section view taken from line 32-32 in FIG. 31 and depicted at a larger scale.

Referring to FIGS. 30-32, a wound retraction device 250 includes an outer ring 252 having a substantially annular shape with an adjustable circumference and a substantially tubular structure 254 extending distally from the outer ring. The outer ring 252 is divided into a plurality of curved ring segments 256 with adjacent curved ring segments being coupled together by means for adjusting the circumference, such as a ratcheting mechanism 258, to form the annular shape. Each of the curved ring segments 256 includes a first, proximal side 260, a second, distal side 262, a first end 264 about the circumference of the outer ring 252 and a second end 266 about the circumference of the outer ring. The curved ring segments 256 may be flexible to maintain a substantially circumferential shape of the outer ring 252 as the diameter of the outer ring is adjusted.

The ratcheting mechanism 258 may include a groove 268 in the proximal surface 260 of each of the curved ring segments 256. The groove 268 substantially follows the curve of the curved ring segment 256 and is opened to the first end 264 of the curved ring segment. The groove 268 includes a plurality of ratchet teeth 270 positioned, for example, on a first, outer curved surface 272 of the groove. Alternatively, the ratchet teeth 270 may be positioned on a second, inner curved surface 274 of the groove 268 or on the distal surface 276 of the groove. The groove 268 may also include a retention channel 278 in at least one of the outer and inner curved surfaces 272, 274 of the groove.

Each of the curved ring segments 256 also includes a flexible, elongate protuberance 280 extending from the second end 266 of the curved ring segment adapted to mate with the groove 268 in an adjacent curved ring segment. The elongate protuberance 280 includes at least one ratchet tooth 282 that interacts with the ratchet teeth 270 in the groove 268 of the curved ring segment 256 adjacent the elongate protuberance. Forming the outer ring 252 includes aligning the curved ring segments 256 together circumferentially with the first end 264 of each of the curved ring segments positioned adjacent the second end 266 of an adjacent curved ring segment and inserting the elongate protuberance 280 of each of the curved ring segments into the groove 268 of the other adjacent curved ring segment such that the at least one ratchet tooth 282 on the elongate protuberance interacts with the ratchet teeth 270 in the groove.

To substantially prevent the elongate protuberance 280 of one curved ring segment 256 from inadvertently slipping out of the groove 268 of the adjacent curved ring segment, the elongate protuberance may include a lip 284 (FIG. 32) extending longitudinally along the length of the elongate protuberance and adapted to interact with the retention channel 278 in the groove of the adjacent curved ring segment. The diameter of the outer ring 252 is adjusted by inserting and retracting the elongate protuberances 280 within the grooves 268 of the adjacent curved ring segments 256. The diameter of the outer ring 252 is increased as the curved ring segments 256 are moved further apart and the diameter is decreased as the curved ring segments are moved closer together.

As with the outer ring 252, the substantially tubular structure 254 is also divided into a plurality of elongate tube segments 286 with each of the tube segments being coupled to a respective curved ring segment 256 and extending distally from the respective curved ring segment. The tube segments 286 may each extend circumferentially between the first end 264 and the second end 266 of the curved ring segment 256 to which the respective tube segment is coupled (FIG. 30) such that there is no overlap between adjacent tube segments. Alternatively, each of the tube segments 286 may extend circumferentially beyond at least one of the first and second ends 264, 266 of the curved ring segment to which the respective tube segment is coupled (FIG. 31) such that adjacent tube segments may overlap each other. The profile of the tube segments 286 may substantially follow the curve of the curved ring segment 256 to which the respective tube segment is coupled. The tube segments 286 may be flexible so as to follow any change of the curve of the curved ring segments 256 to which the respective tube segments are coupled. The tube segments 286 may be made of a biocompatible material, such as a metallic or polymeric material.

Referring to FIG. 31, the retraction ring 250 may include an inner ring 288 that is substantially opposite to the outer ring 252 to maintain the diameter of the tubular structure 254 at the distal end 290 of the tubular structure substantially the same as the diameter at the proximal end 292 of the tubular structure. The inner ring 288 includes the ratcheting mechanism 258, but with the groove 268 positioned on the distal surface of the curved ring segments 256. In use, with both the outer ring 252 and the inner ring 288 retracted to their smallest respective diameters, the distal end 262 of the wound retraction device 250, including the inner ring, may be inserted through a small incision 62 (FIGS. 1 and 2) in a body wall 60 and into a body cavity 52. The inner ring 288 may be expanded to a larger diameter to deploy the inner ring in the form of a distal retention member. With the inner ring 288 deployed, the outer ring 252 may be adjusted to a larger diameter to provide tension upon the tube segments 286, thereby providing circumferential retraction of the incision.

For retraction rings 250 that do not include the inner ring 288, the distal ends 290 of the tube segments 286 may be inserted into the incision 62 and into the body cavity 52. The outer ring 252 may be adjusted to a larger diameter to provide tension upon the tube segments 286, thereby providing circumferential retraction of the incision 62. The tube segments 286 are sufficiently strong to maintain retraction of the incision 62 without substantially deflecting the tube sections.

Figure 33:
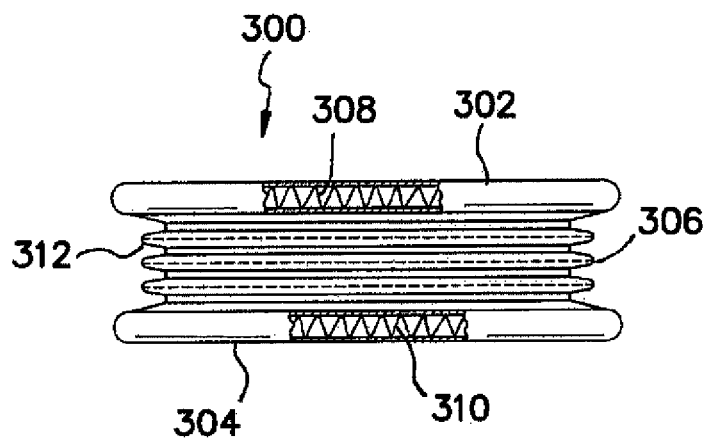
FIG. 33 is a side view of an adjustable wound retraction device having two rings and a sheath comprising bellows in a low profile, insertion condition.
Figure 34:
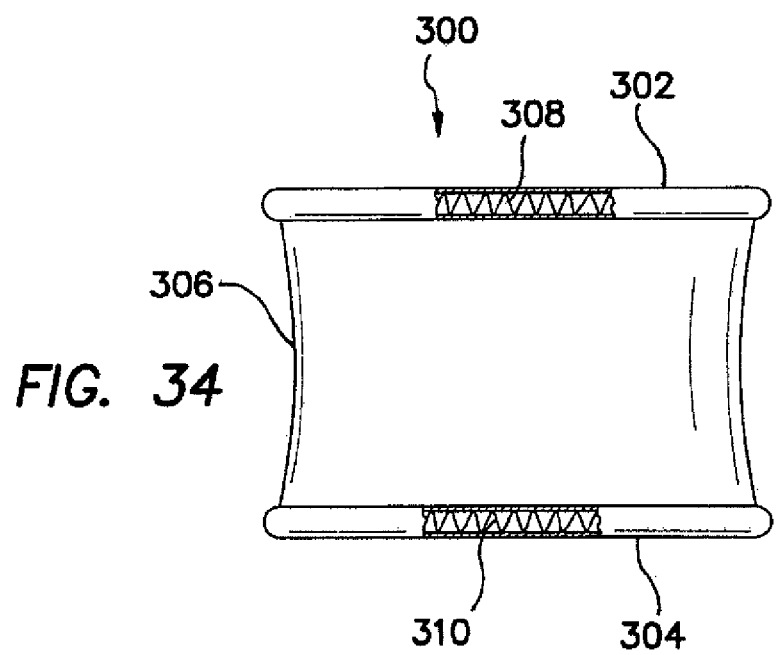
FIG. 34 is a side view of the adjustable wound retraction device of FIG. 33 in a deployed, retracting condition.

Referring to FIGS. 33 and 34 a circumferential surgical retraction device 300 includes a first, substantially annular, outer ring 302 and a second, substantially annular, inner ring 304. The first and second rings 302, 304 are separated by a substantially gastight cylindrical sleeve 306. The first and second rings 302, 304 may be made of a substantially flexible material, such as a polymeric material, and may be reinforced with a first and second biasing member 308, 310, respectively, such as a spring-like core positioned in each of the first and second rings, that biases the first and second rings radially outwardly. Biasing the first and second rings 302, 304 radially outwardly subsequently biases the retraction device 300 toward a shorter axial length. The cylindrical sleeve 306 is coupled to the first and second rings 302, 304. The cylindrical sleeve 306 may include a bellows 312, or radial folds, that allow the cylindrical sleeve to transition between a first, axially compressed state (FIG. 33) and a second, axially extended state (FIG. 34).

With the retraction device 300 in the first, axially compressed state (FIG. 33), the retraction device may be further compressed radially at opposing points along the inner and outer rings 302, 304 to transform the retraction device into a low profile, elongate, oval shape to facilitate insertion into an incision 62 (FIGS. 1 and 2). The retraction device 300 is advanced through the incision 62 until the inner ring 304 is completely within the body cavity 52. The radial compression is released from the inner ring 304 and the inner ring is permitted to assume its substantially circular configuration. The outer ring 302 is pulled proximally through the incision, thereby pulling the inner ring 304 into sealing contact with the inner surface 66 of the body wall 60 and stretching the bellows 312 of the cylindrical sleeve 306. The outer ring 302 is pulled proximally until the outer ring is outside the incision 62 and the retraction device is in the second, axially extended state (FIG. 34). The first biasing member 308 in the outer ring 302 biases the outer ring radially outward and into sealing contact with the outer surface of the body wall 60. With the biasing member 308, 310 in each of the outer and inner rings 302, 304 biasing the rings radially outward, the cylindrical sleeve 306 is placed in tension and retracts the incision 62. Following the surgical procedure, removal of the retraction device 300 is accomplished by reaching into the body cavity 52 and pulling the inner ring 304 proximally through the incision 62, thereby removing the cylindrical sleeve 306 from the incision.

Figure 35:
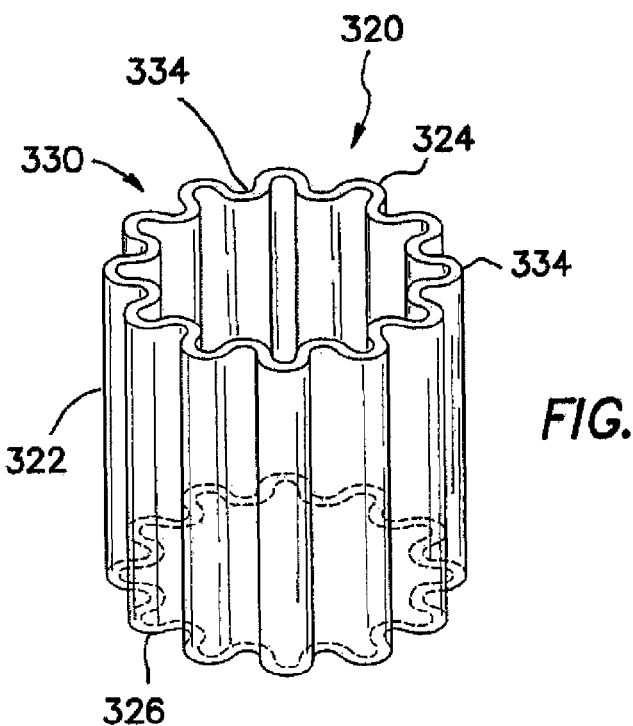
FIG. 35 is a perspective view of a malleable retraction ring in a closed condition for insertion into an incision.
Figure 36:
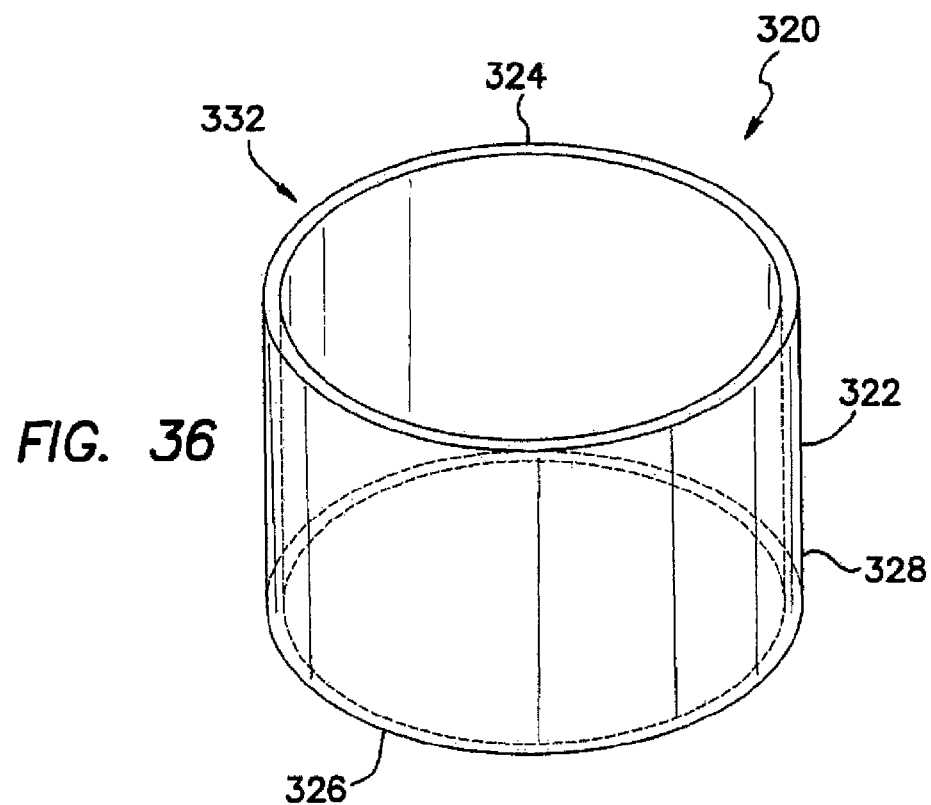
FIG. 36 is a perspective view of the malleable retraction ring of FIG. 35 in a fully open, deployed condition.

Referring to FIGS. 35 and 36, a wound retraction device 320 includes a gastight, tubular membrane or sheath 322 having a first, proximal end 324 and a second, distal end 326. The sheath 322 is sufficiently long to fit completely through a body wall, such as an abdominal wall 60 (FIGS. 1 and 2). The sheath 322 includes a malleable, generally circular member 328 that assumes a first circumference (FIG. 35) when compressed to a first, folded condition 330 and a second, larger circumference (FIG. 36) when unfolded to a second, unfolded condition 332. The sheath 322 is biased toward the second, unfolded condition 332. The sheath 322 may be compressed to the first, folded condition 330 by means of a circularly retracting tool or even by a surgeon's hands. In the first, folded condition 330, the sheath 322 may include undulations 334 about its circumference. When the force holding the sheath 322 in the folded condition 330 is removed, the sheath opens to the second, unfolded condition 332.

In use, the sheath 322 is compressed to the first, folded condition 330 and inserted into an incision 62 in a body wall 60. When the sheath 322 is positioned completely across the body wall 60, the force holding the sheath in the folded condition is removed and the sheath expands to the second, unfolded condition 332 and retracts the incision through which it is placed.

The folded and unfolded conditions of the sheath 322 may represent a détente relationship where the first, folded, condition (FIG. 35) is a relaxed, non-tensioned condition or a compressed condition and where the second, unfolded, condition (FIG. 36) is a fixed, over-centered, condition having sufficient hoop strength to resist compression or refolding. The sheath 322 in the second unfolded condition 332 may include means to prevent the sheath from shifting position within the retracted wound, such as undulations or protrusions on the outer surface of the sheath. Alternate embodiments may include midpoint conditions between a first, folded condition and a second, unfolded condition.

Figure 37:
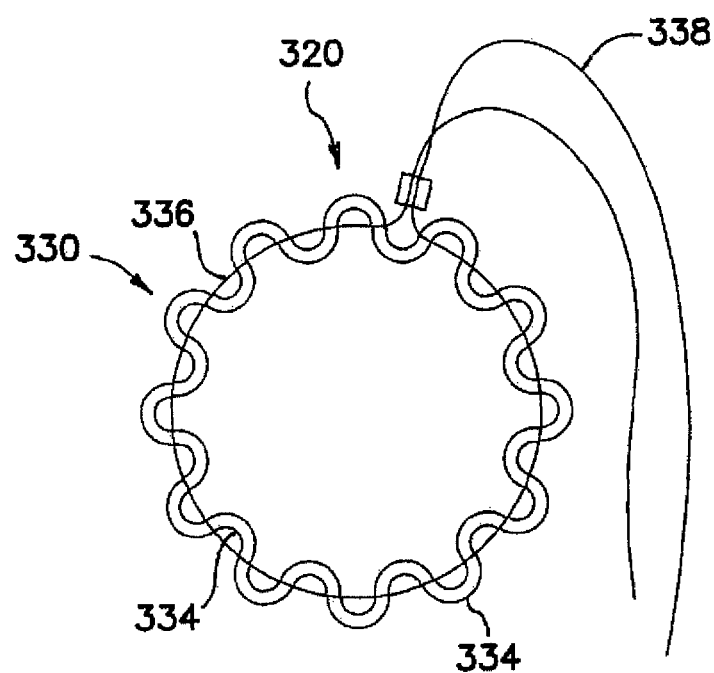
FIG. 37 is a plan view of the malleable retraction ring of FIG. 35 in a closed condition for insertion into an incision with the retraction ring being held closed by a drawstring.
Figure 38:
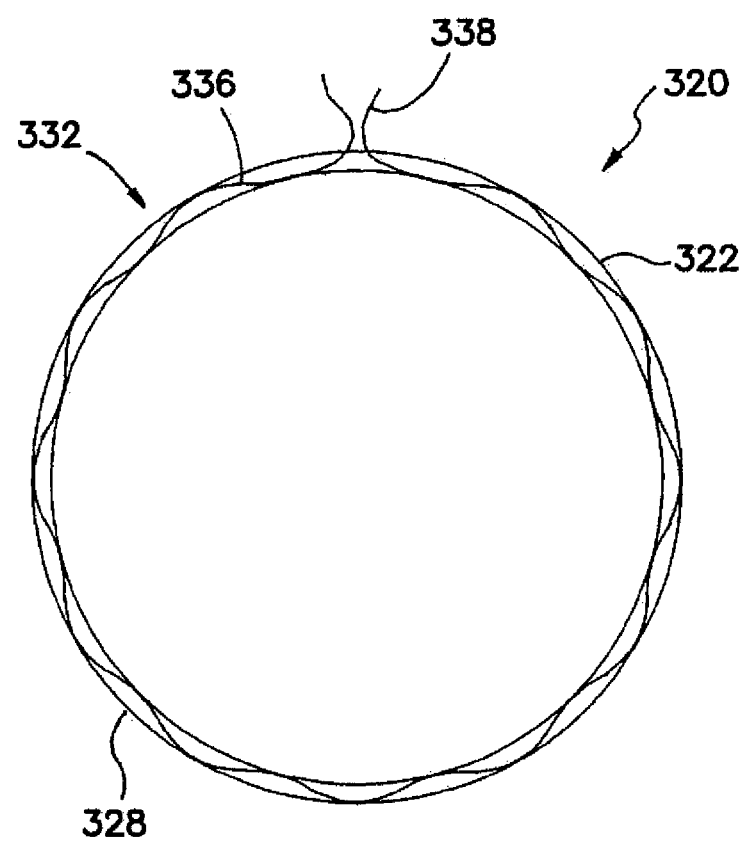
FIG. 38 is a perspective view of the malleable retraction ring of FIG. 37 in a fully open, deployed condition.

Referring to FIG. 37, the wound retraction device 320 of FIGS. 35 and 36 may include means for compressing the sheath 322 into the first, folded condition 330. Such means may include a drawstring 336. The drawstring 336 may include a flexible string 338 that is threaded through the undulations 334 of the sheath 322. The string 338 may include cord, twine, cable, thread, or similar materials that are well known in the art. To compress the sheath 322 into the first, folded condition 330, the drawstring 336 is pulled radially away from the sheath. When the drawstring 336 is released (FIG. 38), the sheath 322 assumes the second, unfolded condition 332.

Figure 39:
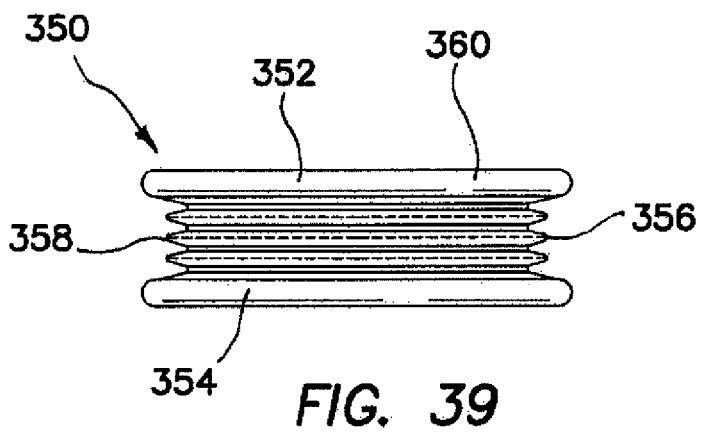
FIG. 39 illustrates an expandable and retractable anchoring ring having inflatable portions in a low profile, uninflated, insertion condition.
Figure 40:
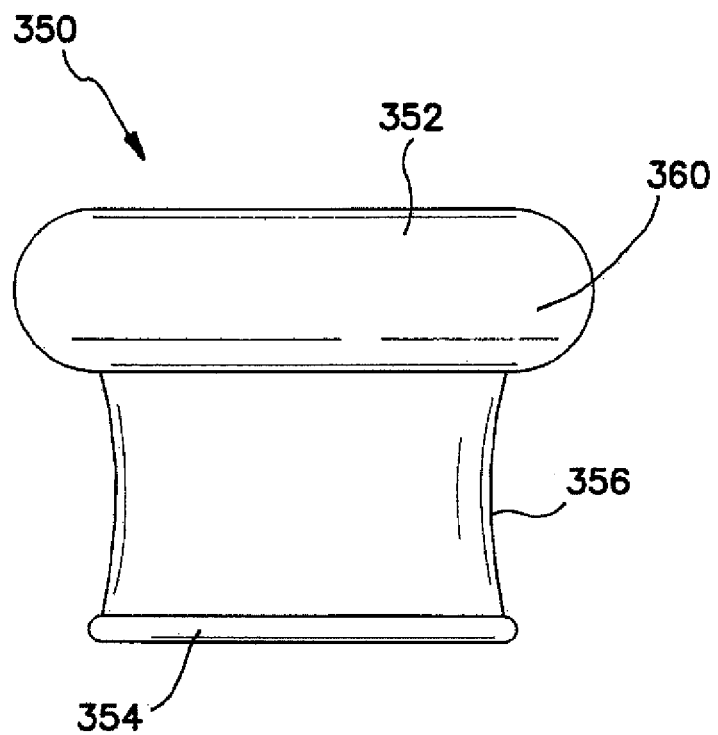
FIG. 40 illustrates the expandable and retractable anchoring ring of FIG. 39 in an inflated, deployed condition.

Referring to FIGS. 39 and 40, a circumferential retraction device 350 includes a first, outer retention ring 352, a second, inner, flexible or shapeable retention ring 354 and a gastight, substantially cylindrical sleeve 356 coupled to the first and second rings. The outer retention ring 352 is sized and configured to remain outside a body cavity 52. The inner retention ring 354 is sized and configured for insertion into and through a surgical incision 62 in a body wall 60 and into the body cavity 52. The cylindrical sleeve 356 is configured to be tensioned between the first ring 352 and the second ring 354 to retract the incision 62 in the body wall 60. The cylindrical sleeve 356 may include a bellows 358, or radial folds, that allow the cylindrical sleeve to transition between a first, axially compressed state (FIG. 39) and a second, axially extended state (FIG. 40).

With the retraction device 350 in the first, axially compressed state (FIG. 39), the second, inner retention ring 354 may be compressed radially at opposing points along its circumference to transform the circular second retention ring into an elongate, oval shape to facilitate insertion into an incision 62 (FIGS. 1 and 2). The second ring 354 is advanced through the incision 62 until it is completely within the body cavity 52. The radial compression is released from the second ring 354 and the second ring is permitted to assume its substantially circular configuration. The first ring 352 includes a substantially hollow, inflatable structure 360 that may be enlarged by pressurization with gas or fluid. With the retraction device 350 positioned in the incision 62, the first, outer ring 352 may be inflated (FIG. 40), thereby placing increasing tension on the gastight sleeve 356. Since the second, inner ring 354 cannot be drawn into the incision, the increasing tension on the sleeve 356 retracts and enlarges the incision through which it extends.

It will be understood that many modifications can be made to the disclosed embodiments without departing from the spirit and scope of the invention. For example, various sizes of the surgical device are contemplated as well as various types of constructions and materials. It will also be apparent that many modifications can be made to the configuration of parts as well as their interaction. For these reasons, the above description should not be construed as limiting the invention, but should be interpreted as merely exemplary of the embodiments.

The invention claimed is:

1. A retraction device for retracting an incision in a body wall, the retraction device comprising:
   a first, distal retention ring;
   a second, proximal retention ring;
   a circumferential, tubular sheath coupled to the first and second retention rings, the sheath having a lumen;
   a plurality of tensioning straps, each of the plurality of straps being coupled to the distal retention ring and extending proximally through the lumen of the sheath and the proximal retention ring; and
   a proximal lock ring being sized and configured to capture the straps between an inner surface of the proximal retention ring and an outer surface of the lock ring, the lock ring being adapted to be positioned within a lumen of the proximal retention ring with the straps exiting between the proximal retention ring and the lock ring,
   wherein the straps being adapted to be pulled proximally to achieve appropriate tension and subsequent retraction of the incision, and
   the lock ring responding to the tension of the straps by wedging against the inner surface of the proximal retention ring and substantially preventing the straps from slipping distally between the lock ring and the proximal retention ring.

2. The retraction device of claim 1, at least one of the inner surface of the proximal retention ring and the outer surface of the lock ring being beveled.

3. The retraction device of claim 1, each of the plurality of straps being formed of a strong, thin, non-elastic material.

4. The retraction device of claim 1, wherein release of tension of the plurality of straps being accomplished by pulling at least one of the tensioned straps proximally slightly to release the lock ring from the proximal ring and removing the lock ring.

5. The retraction device of claim 1, wherein the distal retention ring comprises a shapeable material.

6. The retention device of claim 5, wherein the distal retention ring may be deformed for insertion into a body cavity through an incision in a body wall.

7. The retraction device of claim 1, wherein the proximal retention ring comprises a material more rigid than the material of the distal retention ring.

* * * * *